(12) United States Patent
Inuzuka et al.

(10) Patent No.: US 9,867,534 B2
(45) Date of Patent: Jan. 16, 2018

(54) OPHTHALMOLOGIC APPARATUS AND OPHTHALMOLOGIC APPARATUS SYSTEM

(71) Applicant: TOPCON CORPORATION, Itabashi-ku (JP)

(72) Inventors: Naoki Inuzuka, Arakawa-ku (JP);
Tomohiro Sakurada, Itabashi-ku (JP);
Naoki Kaneda, Kawaguchi (JP)

(73) Assignee: TOPCON CORPORATION, Itabashi-ku (JP)

( * ) Notice: Subject to any disclaimer, the term of this patent is extended or adjusted under 35 U.S.C. 154(b) by 93 days.

(21) Appl. No.: 15/131,329

(22) Filed: Apr. 18, 2016

(65) Prior Publication Data

US 2016/0317022 A1 Nov. 3, 2016

(30) Foreign Application Priority Data

Apr. 30, 2015 (JP) ................. 2015-093717
Apr. 30, 2015 (JP) ................. 2015-093718
Apr. 30, 2015 (JP) ................. 2015-093719

(51) Int. Cl.
*A61B 3/14* (2006.01)
*A61B 3/00* (2006.01)
*A61B 3/15* (2006.01)

(52) U.S. Cl.
CPC .......... *A61B 3/0033* (2013.01); *A61B 3/0041* (2013.01); *A61B 3/0075* (2013.01); *A61B 3/152* (2013.01)

(58) Field of Classification Search
CPC ........ A61B 3/0033; A61B 3/0041; A61B 3/14
USPC .................................. 351/205, 206, 208
See application file for complete search history.

(56) References Cited

FOREIGN PATENT DOCUMENTS

| JP | 3676053 | 7/2005 |
|---|---|---|
| JP | 2008-61715 | 3/2008 |
| JP | 2009-66025 | 4/2009 |
| JP | 2012-148030 | 8/2012 |
| JP | 2015-58107 | 3/2015 |

*Primary Examiner* — Jack Dinh
(74) *Attorney, Agent, or Firm* — Oblon, McClelland, Maier & Neustadt, L.L.P.

(57) ABSTRACT

According to one embodiment, an ophthalmologic apparatus is configured such that an operation unit is attached thereto. The ophthalmologic apparatus includes a measuring head, a user interface, and a controller. The measuring head is configured to perform optical measurement of a subject's eye. The user interface is used for performing an operation in relation to the optical measurement of the subject's eye. The controller is configured to detect whether an operation on the operation unit is enabled. Further, the controller is configured to perform at least display control for the user interface in different operation modes between an enabled state in which the operation on the operation unit is enabled and a disabled state in which the operation on the operation unit is disabled.

9 Claims, 32 Drawing Sheets

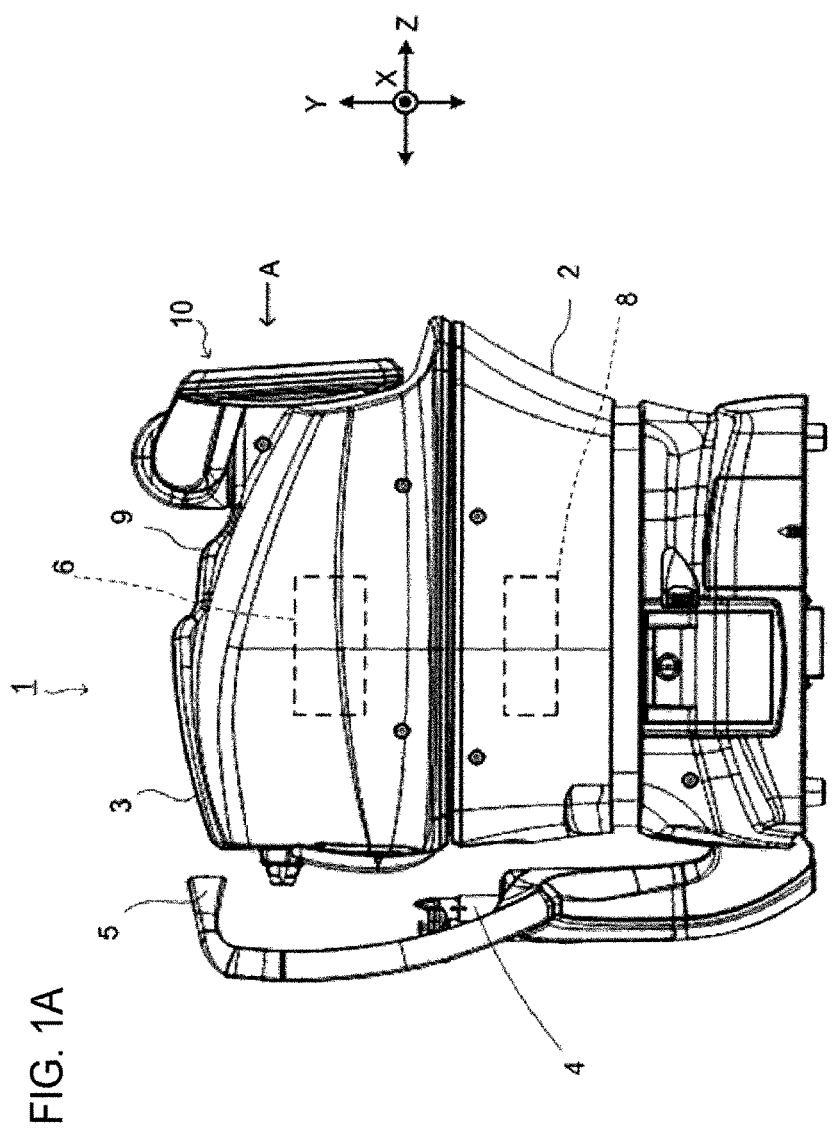

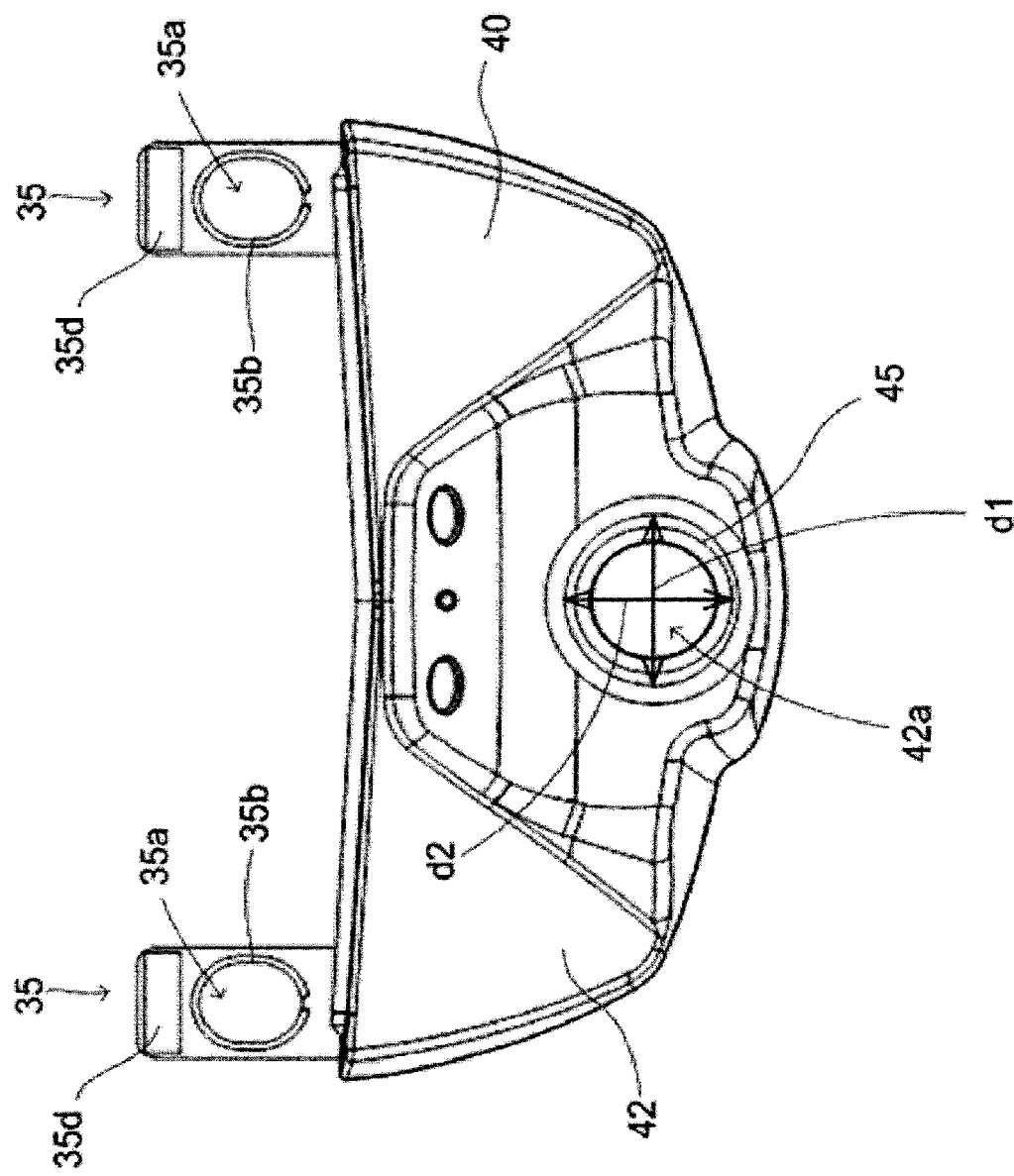

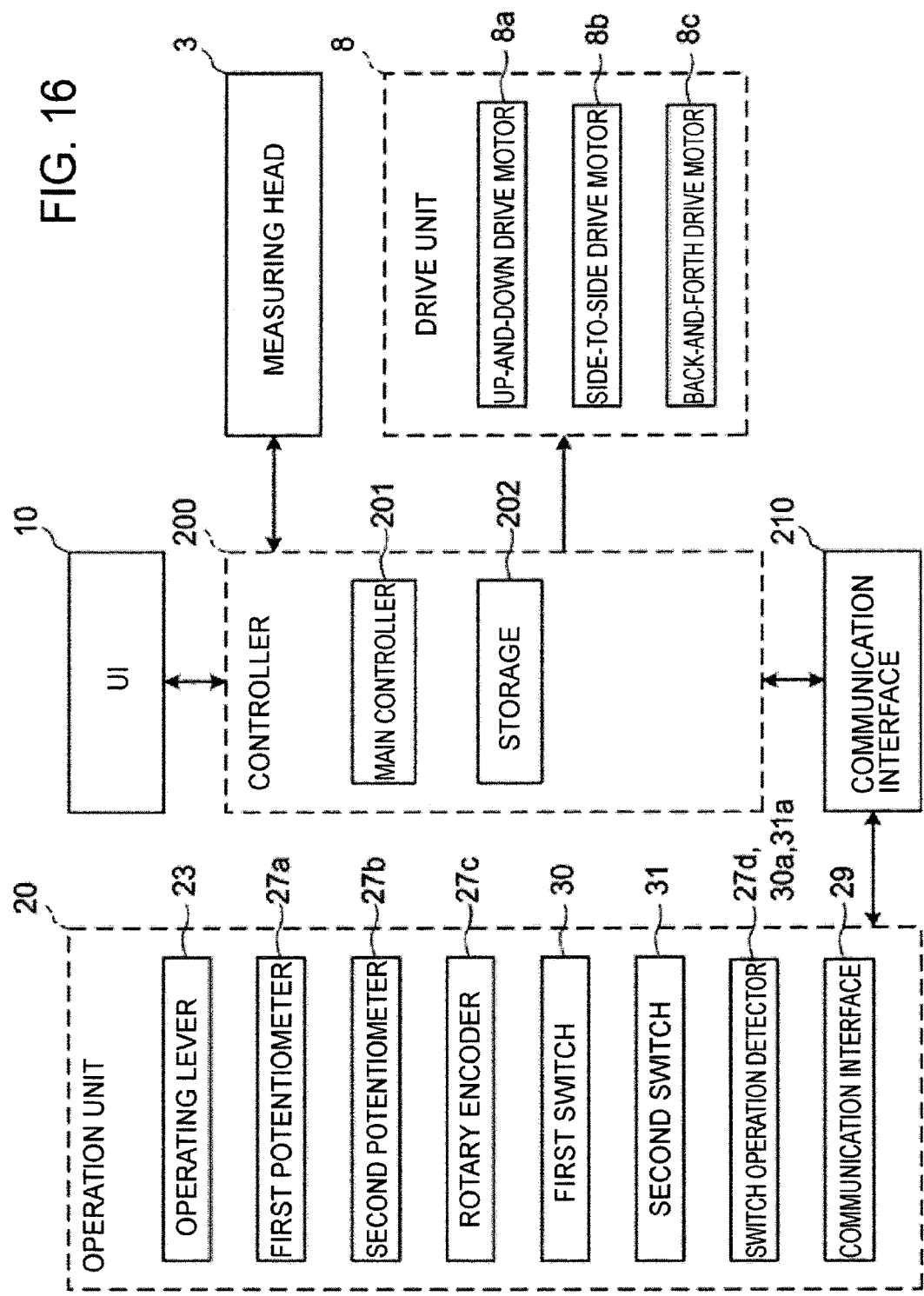

OPHTHALMOLOGIC APPARATUS AND OPHTHALMOLOGIC APPARATUS SYSTEM

CROSS-REFERENCE TO RELATED APPLICATIONS

This application is based upon and claims the benefit of priority from Japanese Patent Applications No. 2015-093717, filed 30 Apr. 2015; No. 2015-093718, filed 30 Apr. 2015; and No. 2015-093719, filed 30 Apr. 2015; the entire contents of which are incorporated herein by reference.

FIELD

Embodiments described herein relate generally to an ophthalmologic apparatus and an ophthalmologic apparatus system.

BACKGROUND

An ophthalmologic apparatus is capable of photographing a subject's eye or measuring the characteristics of the subject's eye using an optical system. Generally, the ophthalmologic apparatus includes a measuring head that is movable in the lateral direction, vertical direction, and front-back direction relative to the base, and an operation unit for moving the measuring head. The measuring head is provided with an optical system for measuring the characteristics of the subject's eye or capturing an image of the subject's eye, and an alignment unit or the like for aligning the optical system with respect to the subject's eye. In response to an operation performed on the operation unit, the ophthalmologic apparatus moves the measuring head to perform a measurement at a position where the measuring head has been moved.

For example, Japanese Patent No. 3676053 discloses an ophthalmologic apparatus, in which a measuring head and an operation and display unit are connected by a cable. The operation and display unit includes a joystick for operating the measuring head and a display for displaying an image of the subject's eye.

If the measuring head and a unit for operation are formed separately, the unit for operation is likely to be provided as optional equipment for a main body including a measuring head. In this case, the examiner or the like is required to know the mounted state of the unit to operate the ophthalmologic apparatus. Especially, if the main body has another operation unit, the examiner or the like may wonder whether to use the operation unit of the main body or the unit for operation as optional equipment, resulting in a prolonged examination time. Further, the examiner or the like may perform an examination while forgetting that the measuring head can also be operated with the unit. In this case, the subject loses the opportunity to be examined with high accuracy by operation on the unit.

SUMMARY

Embodiments are intended to provide an ophthalmologic apparatus and an ophthalmologic apparatus system that changes its operation according to whether an operation unit is attached thereto.

According to one aspect of an embodiment, an ophthalmologic apparatus is configured such that an operation unit is attached thereto. The ophthalmologic apparatus includes a measuring head, a user interface, and a controller. The measuring head is configured to perform optical measurement of a subject's eye. The user interface is used for performing an operation in relation to the optical measurement of the subject's eye. The controller is configured to detect whether an operation on the operation unit is enabled. Further, the controller is configured to perform at least display control for the user interface in different operation modes between an enabled state in which the operation on the operation unit is enabled and a disabled state in which the operation on the operation unit is disabled.

BRIEF DESCRIPTION OF THE DRAWINGS

FIG. 1A is a schematic diagram illustrating an example of the exterior configuration of an ophthalmologic apparatus according to an embodiment;

FIG. 7B is a schematic diagram illustrating an example of the exterior configuration of the operation unit of the embodiment;

FIG. 16 is a schematic diagram illustrating an example of the configuration of a control system in the ophthalmologic apparatus system of the embodiment;

DETAILED DESCRIPTION

Exemplary embodiments of an ophthalmologic apparatus and an ophthalmologic apparatus system are described in detail with reference to the accompanying drawings. The ophthalmologic apparatus system of an embodiment includes an ophthalmologic apparatus and an operation unit configured to be attachable to the ophthalmologic apparatus for operating the ophthalmologic apparatus. The ophthalmologic apparatus includes a user interface (UI). In response to the examiner's operation on the UI or the like, the ophthalmologic apparatus alone is capable of performing any subjective test and/or any objective test. Besides, when the operation unit is attached thereto, in response to operation on the UI or the operation unit, the ophthalmologic apparatus is capable of performing any subjective test and/or any objective test.

For example, the ophthalmologic apparatus may be an optometric apparatus (automatic refractor/keratometer) that can perform far vision test, near vision test, contrast test, glare test, and the like as the subjective test, and objective refractive measurement, corneal shape measurement, and the like as the objective test. However, the ophthalmologic apparatus of the embodiment is not limited thereto. The embodiment is applicable to such ophthalmologic apparatus as fundus photographing apparatus, optical coherence tomography (OCT) device, ocular axial length measurement device, tonometer, and the like. The fundus photographing apparatus is used for imaging the fundus. The OCT device is a device for imaging any part of the subject's eye such as the fundus and the anterior segment using OCT. The ocular axial length measurement device is, for example, a device for measuring the distance from the corneal vertex to the anterior surface of the retina as the ocular axial length by irradiating light onto the subject's eye. The tonometer is, for example, an apparatus for measuring the intraocular pressure based on the amount of light returning from the cornea obtained by illuminating the anterior segment of the subject's eye against which compressed air is being blown, and the pressure of the compressed air, and the like.

The front-back direction of the ophthalmologic apparatus is herein defined as Z direction, the lateral direction as X direction, and the vertical direction as Y direction. Incidentally, all publications and references referred to can be incorporated herein by reference.

<Ophthalmologic Apparatus>

Figure 1B:
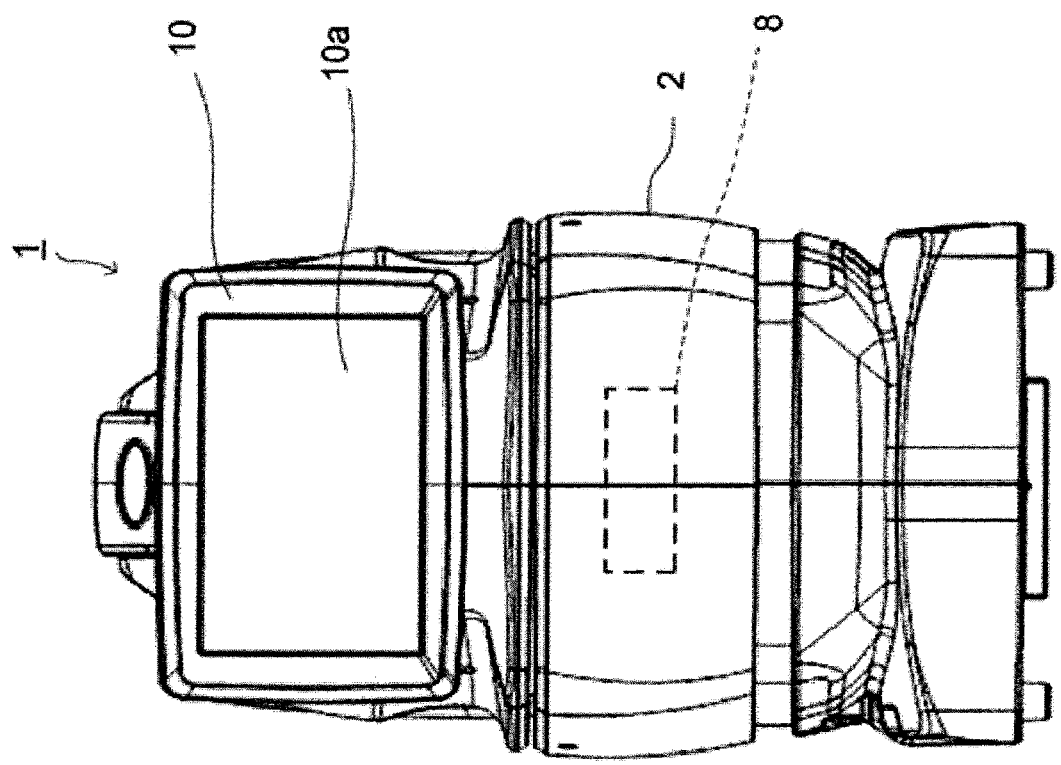
FIG. 1B is a schematic diagram illustrating an example of the exterior configuration of the ophthalmologic apparatus of the embodiment.

FIG. 1A is a schematic diagram illustrating an example of the exterior configuration of an ophthalmologic apparatus 1 according to an embodiment. FIG. 1B is an external view of the ophthalmologic apparatus 1 as viewed from a direction indicated by arrow A shown in FIG. 1A.

The ophthalmologic apparatus 1 includes a base 2, a measuring head 3, a chin rest 4, and a UI 10. The chin rest 4 is provided with a forehead pad 5. The subject takes an examination while placing his/her chin on the chin rest 4 and putting his/her forehead against the forehead pad 5.

The measuring head 3 is provided with a known observation and imaging optical system 6 therein. The observation and imaging optical system 6 is used to observe and photograph the anterior segment, the cornea, the fundus, or the like of the subject's eye. The observation and imaging optical system 6 has a known configuration as described in, for example, Japanese Unexamined Patent Application Publication No. 2015-058107. Accordingly, the configuration of the observation and imaging optical system 6 is not described herein.

The base 2 is provided with a known drive unit 8 for driving the measuring head 3. The drive unit 8 includes, for example, a movement mechanism that moves the measuring head 3 in at least one of the vertical direction, the lateral direction, and the front-back direction, and a drive motor that drives the movement mechanism. In this embodiment, the drive unit 8 includes an up-and-down movement mechanism, a side-to-side movement mechanism, a back-and-forth movement mechanism, an up-and-down drive motor, a side-to-side drive motor, and a back-and-forth drive motor. The up-and-down movement mechanism moves the measuring head 3 up and down. The up-and-down drive motor drives the up-and-down movement mechanism. The side-to-side movement mechanism moves the measuring head 3 side to side. The side-to-side drive motor drives the side-to-side movement mechanism. The back-and-forth movement mechanism moves the measuring head 3 back and forth. The back-and-forth drive motor drives the back-and-forth movement mechanism. The drive unit 8 has a known configuration as described in, for example, Japanese Unexamined Patent Application Publication No. 2008-61715. Therefore, the configuration of the drive unit 8 is not described in detail herein. As being driven by the drive unit 8, the measuring head 3 is moved in the up, down, left, right, forward and backward directions relative to the base 2. This changes the position of the measuring head 3 with respect to the subject's face held by the chin rest 4.

The UI 10 may include a flat panel display such as a liquid crystal display. The UI 10 includes a display screen 10a of a touch panel. The UI 10 is capable of displaying an operation screen, images of the subject's eye, examination results, and the like on the display screen 10a. The UI 10 is configured to allow touch operation on the display screen 10a. When touch operation is performed on the display screen 10a, the measuring head 3 is moved in the up, down, left, right, forward and backward directions with respect to the subject's eye so that the subject's eye can be optically measured.

For presenting the operation screen or the like for the examiner at any position, the position of the UI 10 is variable. FIG. 1A is an external view of the ophthalmologic apparatus for explaining the position of the UI 10 when the examiner conducts a test while facing the subject.

The UI 10 is attached to a top portion 9 of the measuring head 3 to be rotatable in the horizontal and vertical directions. If the rotation of the UI 10 reverses the up/down or left/right direction of the display screen 10a, the ophthalmologic apparatus 1 can control image information so that the image is displayed in the same position on the display screen 10a as viewed before and after the rotation. For example, in response to the rotation of the UI 10, the ophthalmologic apparatus 1 controls image data to reverse the up/down or left/right direction thereof. The configuration and control operation of the ophthalmologic apparatus 1 is known, and the details are described in, for example, Japanese Unexamined Patent Application Publication No. 2012-148030. Accordingly, the specific configuration and control operation of the ophthalmologic apparatus 1 are not described in detail herein.

Figure 2A:
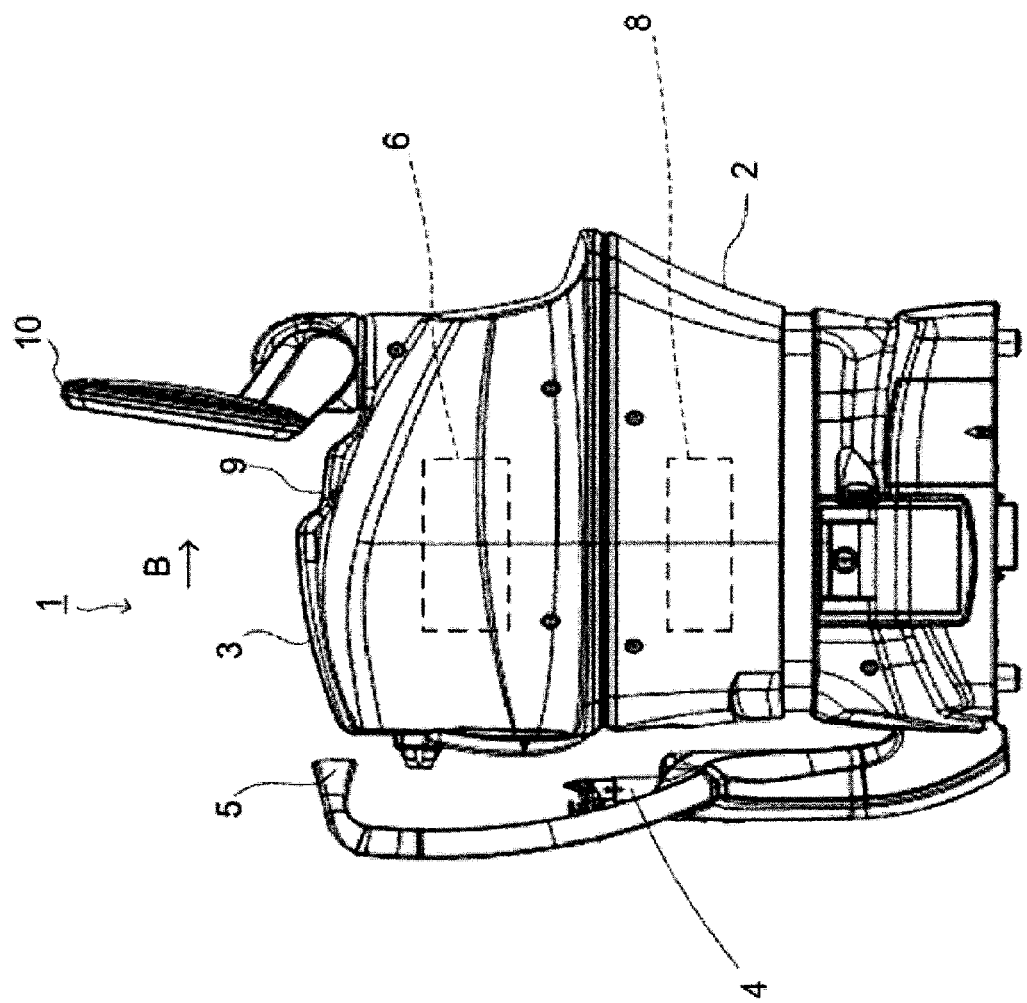
FIG. 2A is a schematic diagram illustrating an example of the exterior configuration of the ophthalmologic apparatus of the embodiment.
Figure 2B:
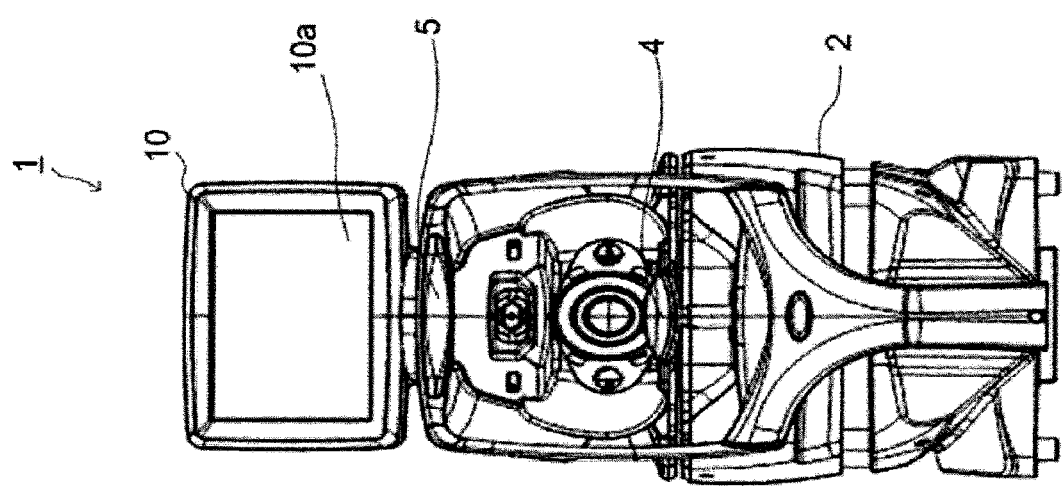
FIG. 2B is a schematic diagram illustrating an example of the exterior configuration of the ophthalmologic apparatus of the embodiment t.

FIG. 2A is an external view of the ophthalmologic apparatus 1 for explaining the position of the UI 10. FIG. 2B is an external view of the ophthalmologic apparatus 1 as viewed from a direction indicated by arrow B shown in FIG. 2A. For example, by changing the position of the UI 10 as illustrated in FIGS. 2A and 2B, the examiner can conduct a test as being close to the subject.

Figure 3A:
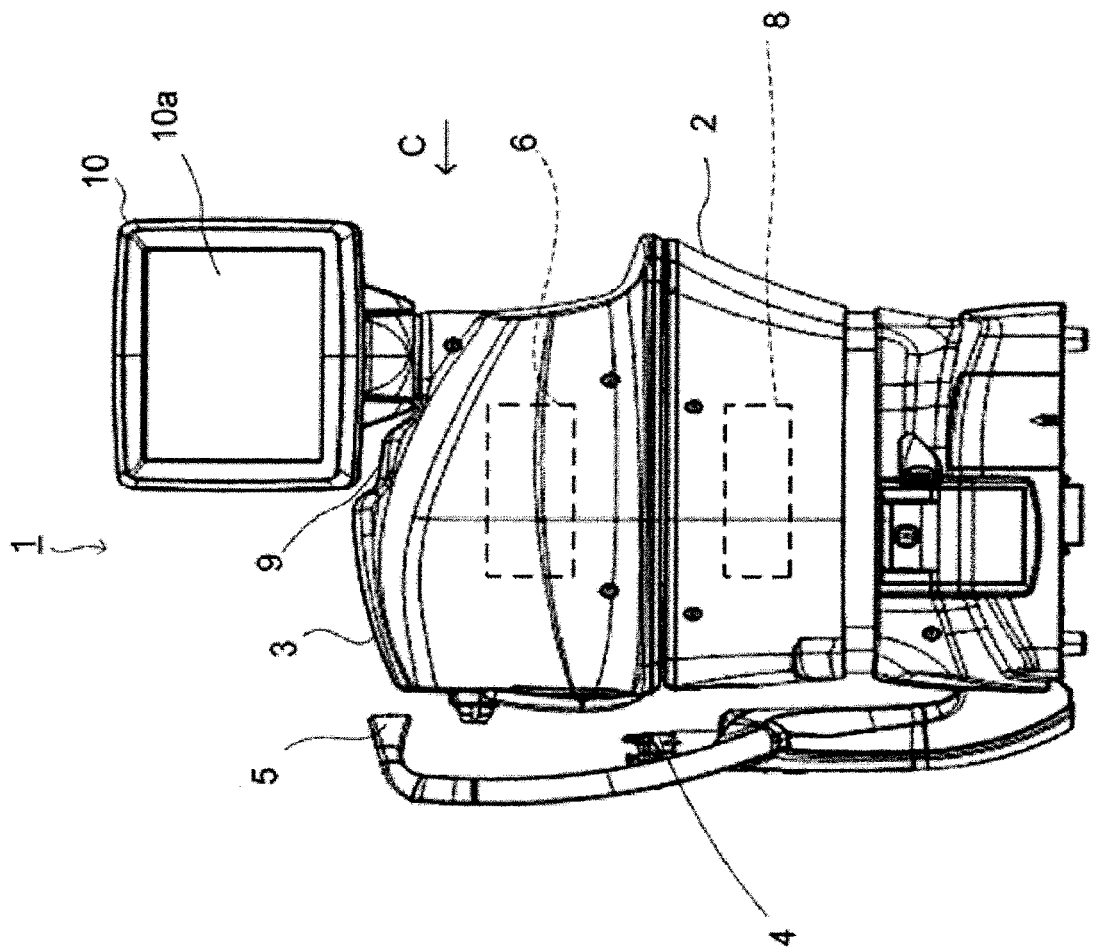
FIG. 3A is a schematic diagram illustrating an example of the exterior configuration of the ophthalmologic apparatus of the embodiment.
Figure 3B:
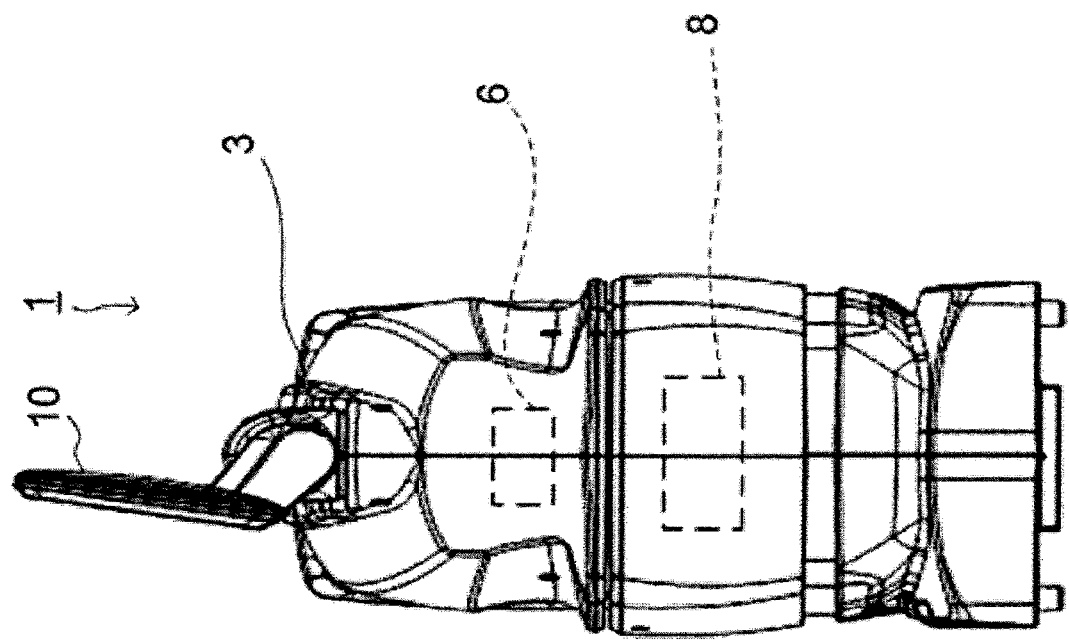
FIG. 3B is a schematic diagram illustrating an example of the exterior configuration of the ophthalmologic apparatus of the embodiment.

FIG. 3A is an external view of the ophthalmologic apparatus 1 for explaining the position of the UI 10. FIG. 3B is an external view of the ophthalmologic apparatus 1 as viewed from a direction indicated by arrow C shown in FIG. 3A. For example, by changing the position of the UI 10 as illustrated in FIGS. 3A and 3B, the examiner can conduct a test as standing on the side of the ophthalmologic apparatus 1.

Figure 4A:
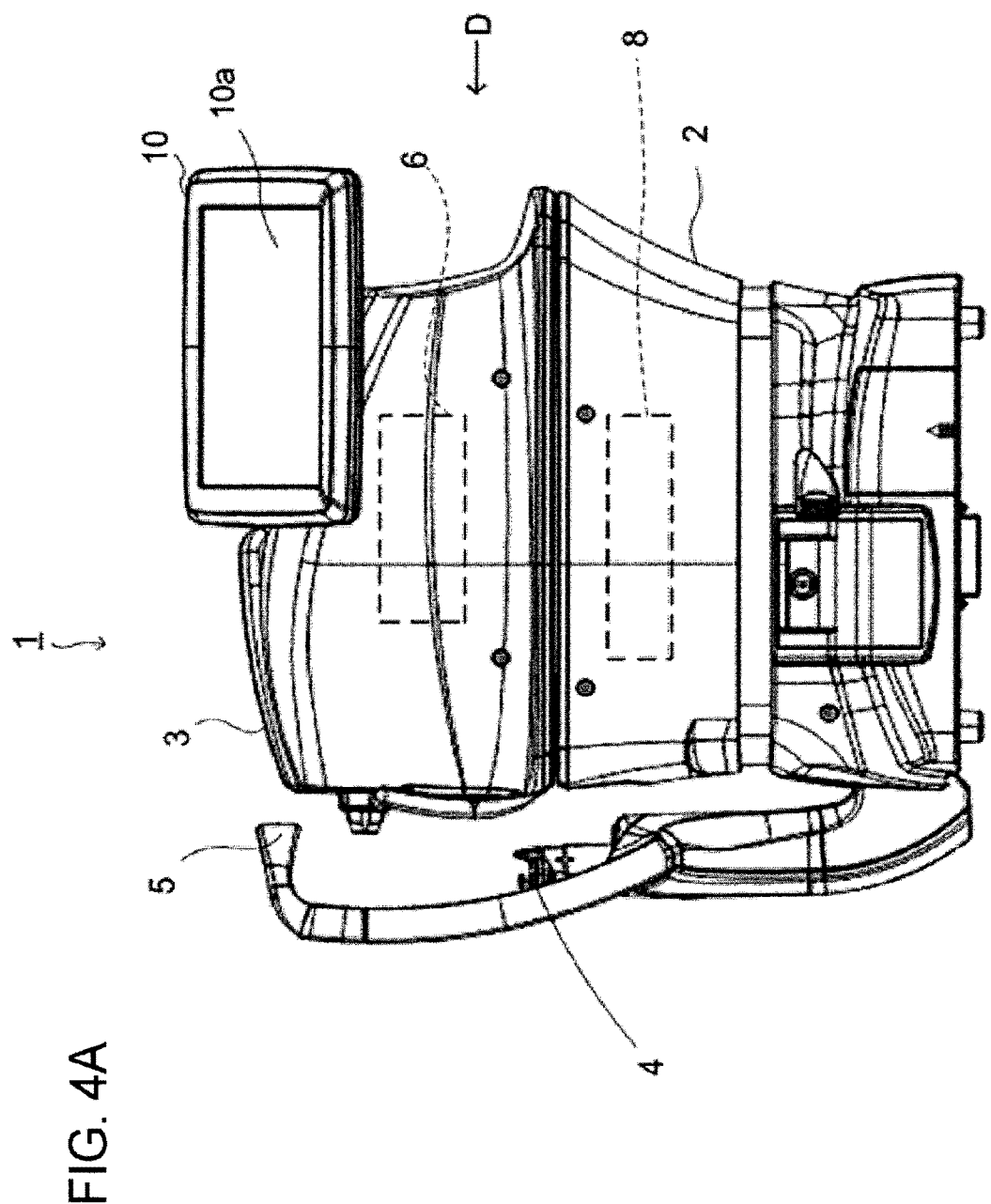
FIG. 4A is a schematic diagram illustrating an example of the exterior configuration of the ophthalmologic apparatus of the embodiment.
Figure 4B:
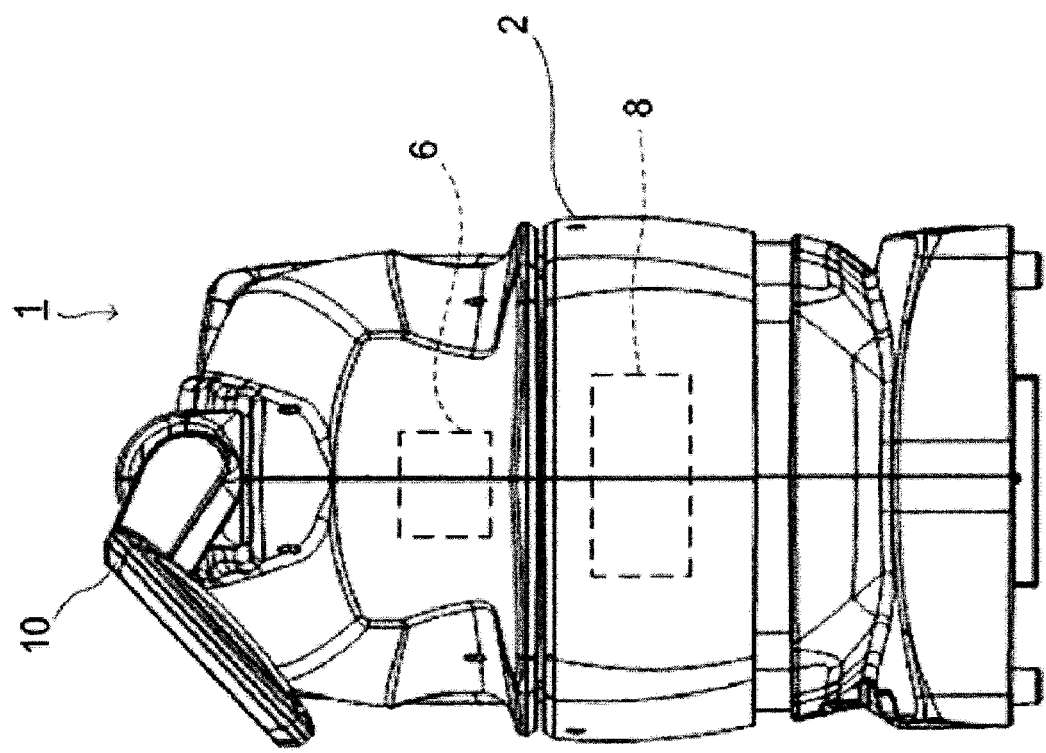
FIG. 4B is a schematic diagram illustrating an example of the exterior configuration of the ophthalmologic apparatus of the embodiment.

FIG. 4A is an external view of the ophthalmologic apparatus 1 for explaining the position of the UI 10. FIG. 4B is an external view of the ophthalmologic apparatus 1 as viewed from a direction indicated by arrow D shown in FIG. 4A. For example, by changing the position of the UT 10 as illustrated in FIGS. 4A and 4B, the examiner can conduct a test as sitting on the side of the ophthalmologic apparatus 1.

Figure 5A:
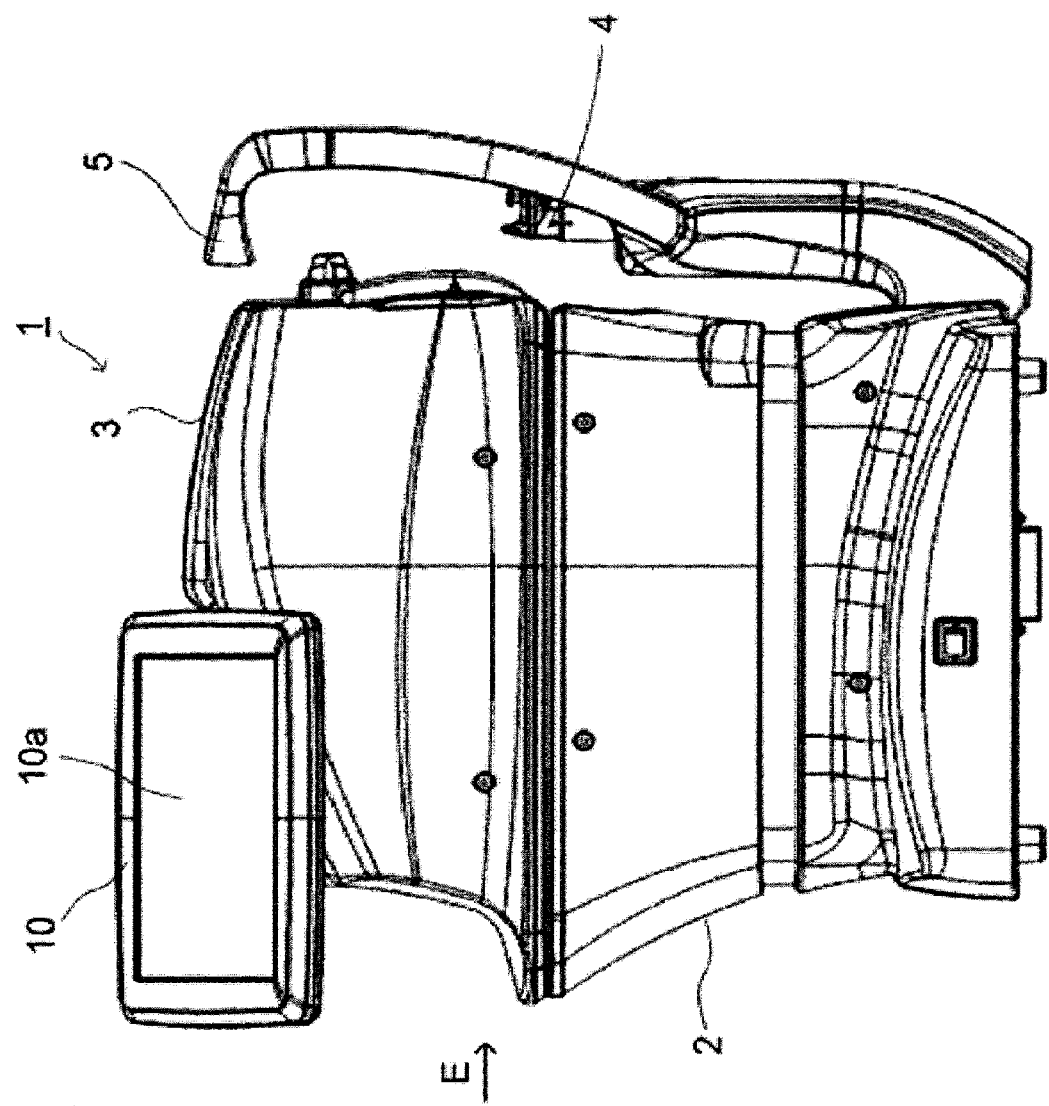
FIG. 5A is a schematic diagram illustrating an example of the exterior configuration of the ophthalmologic apparatus of the embodiment.
Figure 5B:
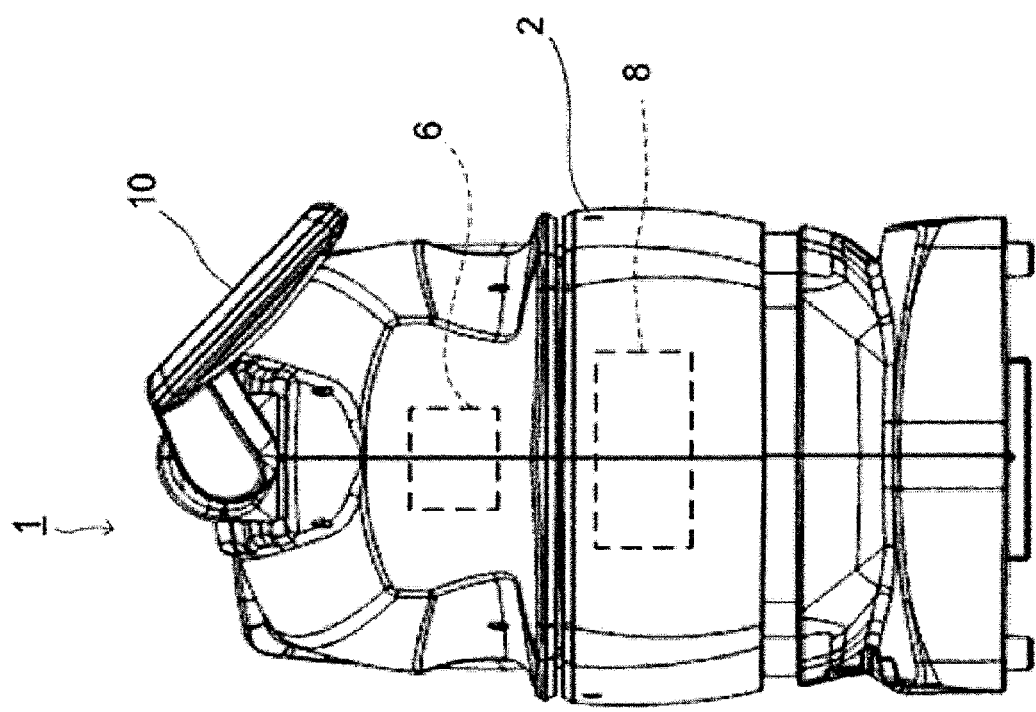
FIG. 5B is a schematic diagram illustrating an example of the exterior configuration of the ophthalmologic apparatus of the embodiment.

FIG. 5A is an external view of the ophthalmologic apparatus 1 for explaining the position of the UI 10. FIG. 5B is an external view of the ophthalmologic apparatus 1 as viewed from a direction indicated by arrow E shown in FIG. 5A. For example, by changing the position of the UI 10 as illustrated in FIGS. 5A and 5B, the examiner can conduct a test as sitting on the side of the ophthalmologic apparatus 1.

As described above, while an image of the subject's eye and the operation screen are being displayed on the UI 10 for the examiner at an any position, the examiner can perform touch operation on the UI 10 at the position to test the subject's eye.

<Operation Unit>

In this embodiment, an operation unit 20 is attached to the ophthalmologic apparatus 1 so that the examiner can perform operation on the operation unit 20 (in particular, tilting the operating lever) at any position. The ophthalmologic apparatus 1 and the operation unit 20 are connected by, for example, a universal serial bus (USB) cable which conforms to the USB standard. The ophthalmologic apparatus 1 supplies power to the operation unit 20 via the USB cable, and transmits a control signal for controlling various detectors (described later). The operation unit 20 includes a control lever and the like. The operation unit 20 sends an operation detection signal corresponding to operation made on the control lever or the like to the ophthalmologic apparatus 1 via the USB cable. Thereby, the skilled examiner, who has been making a fine adjustment by tilting the lever similarly to the conventional manner, can perform operation on the ophthalmologic apparatus 1 at any position without impairing the operability.

Figure 6:
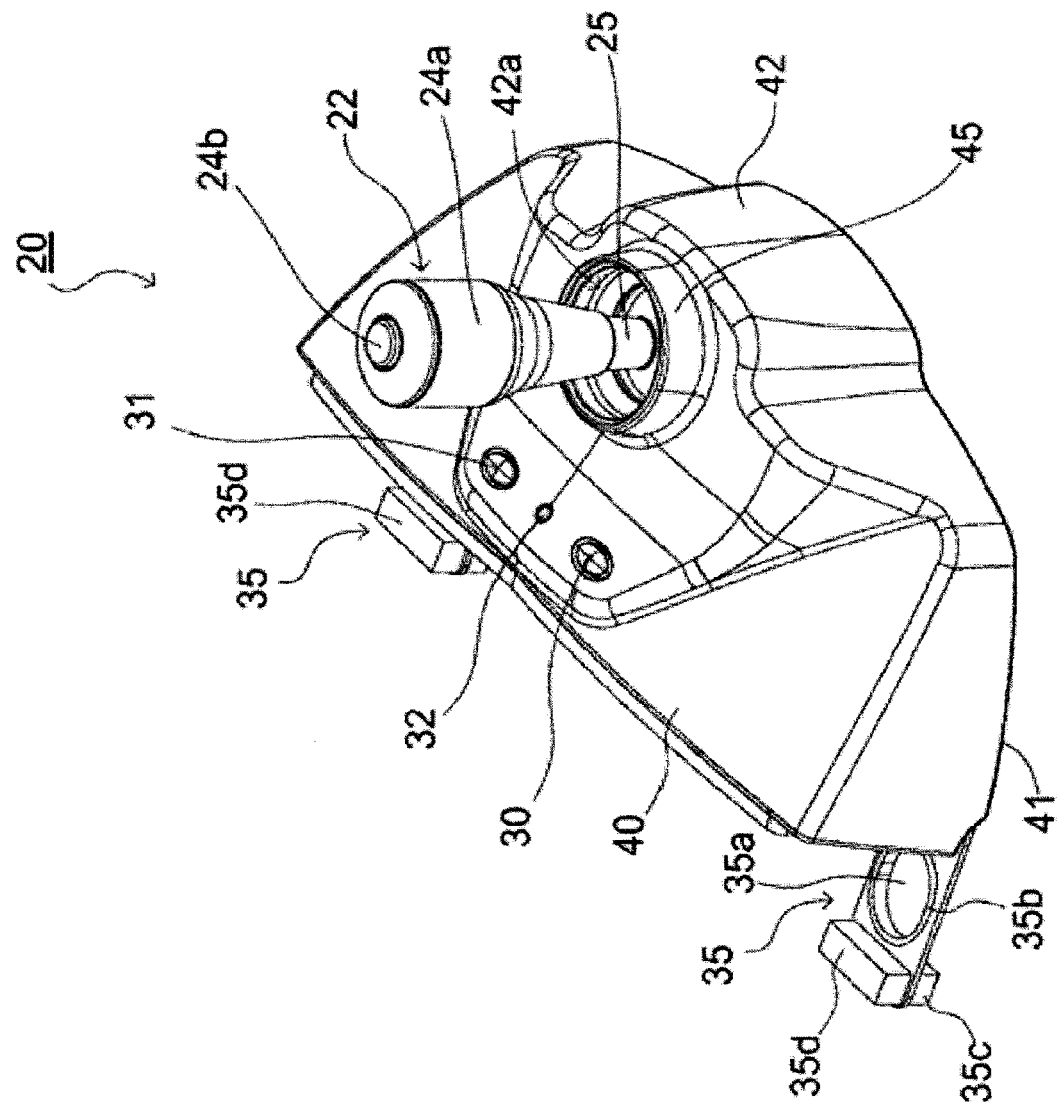
FIG. 6 is a schematic diagram illustrating an example of the exterior configuration of an operation unit of the embodiment.
Figure 7A:
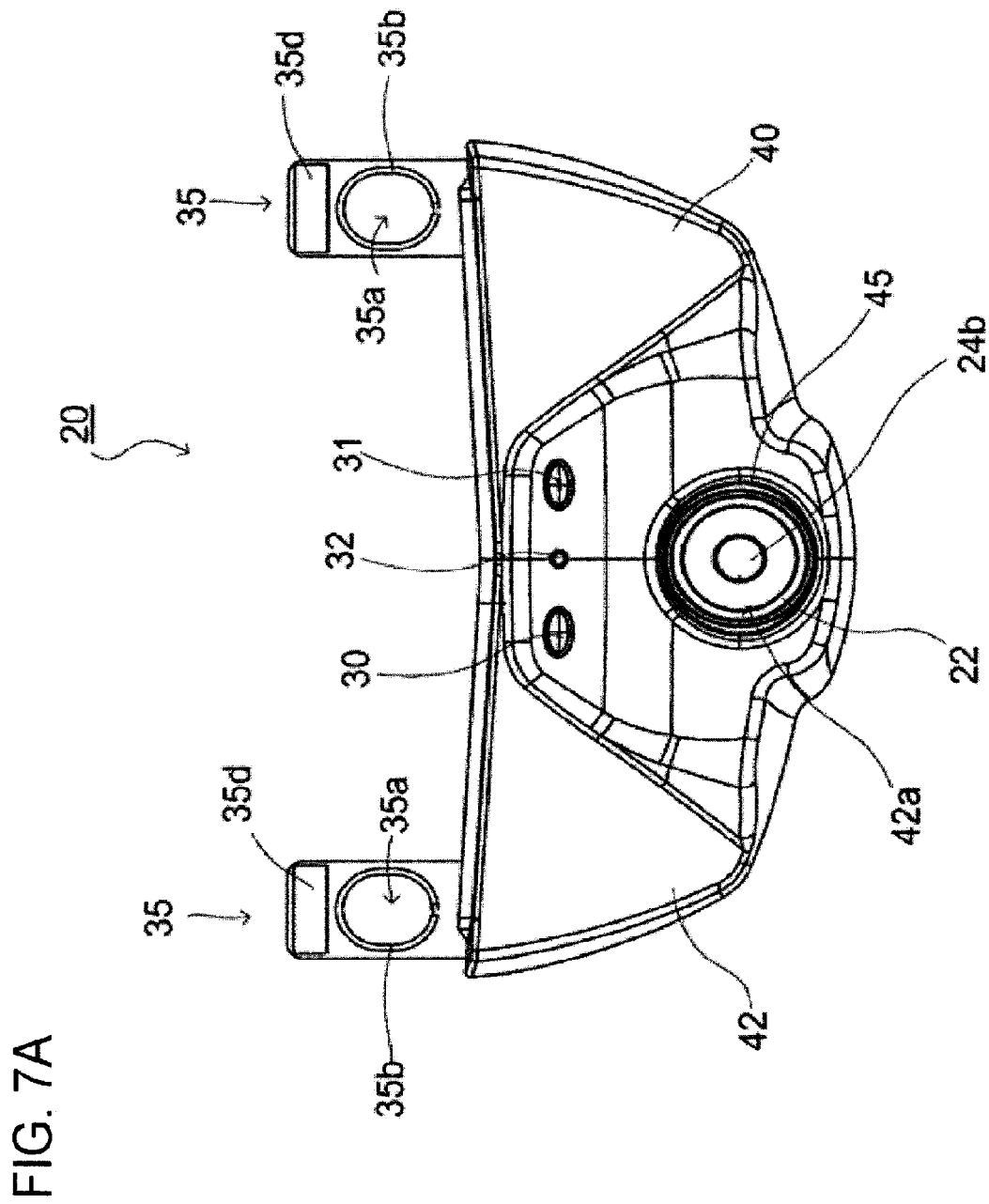
FIG. 7A is a schematic diagram illustrating an example of the exterior configuration of the operation unit of the embodiment.
Figure 8:
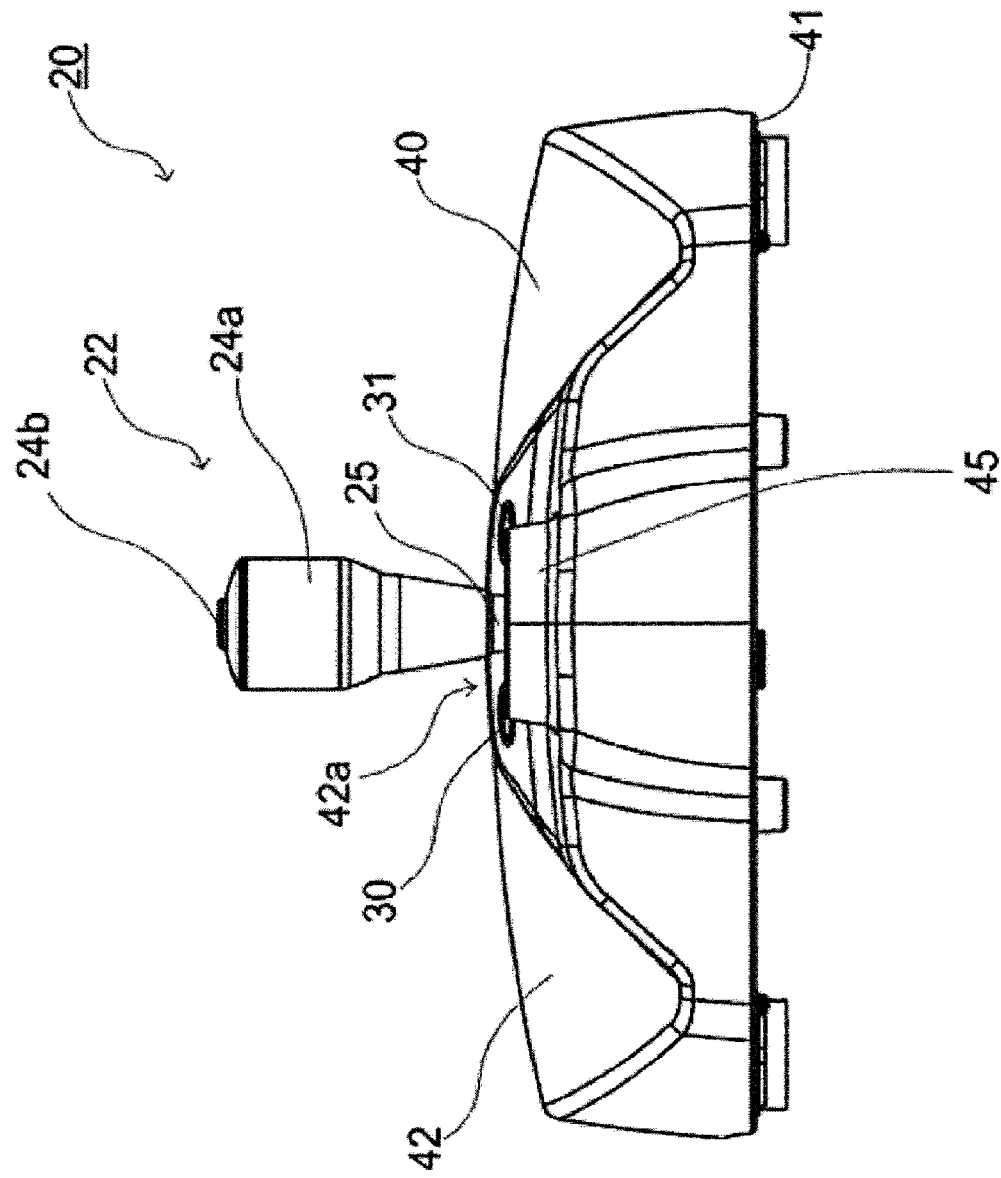
FIG. 8 is a schematic diagram illustrating an example of the exterior configuration of the operation unit of the embodiment.
Figure 9:
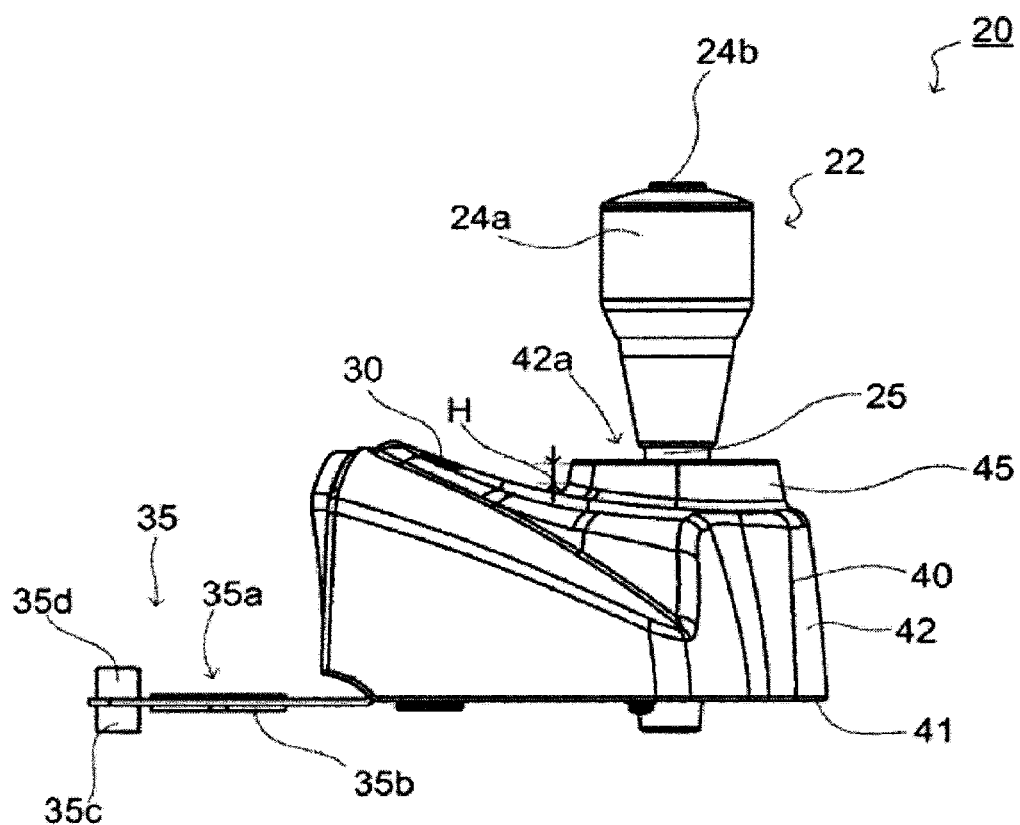
FIG. 9 is a schematic diagram illustrating an example of the exterior configuration of the operation unit of the embodiment.
Figure 10:
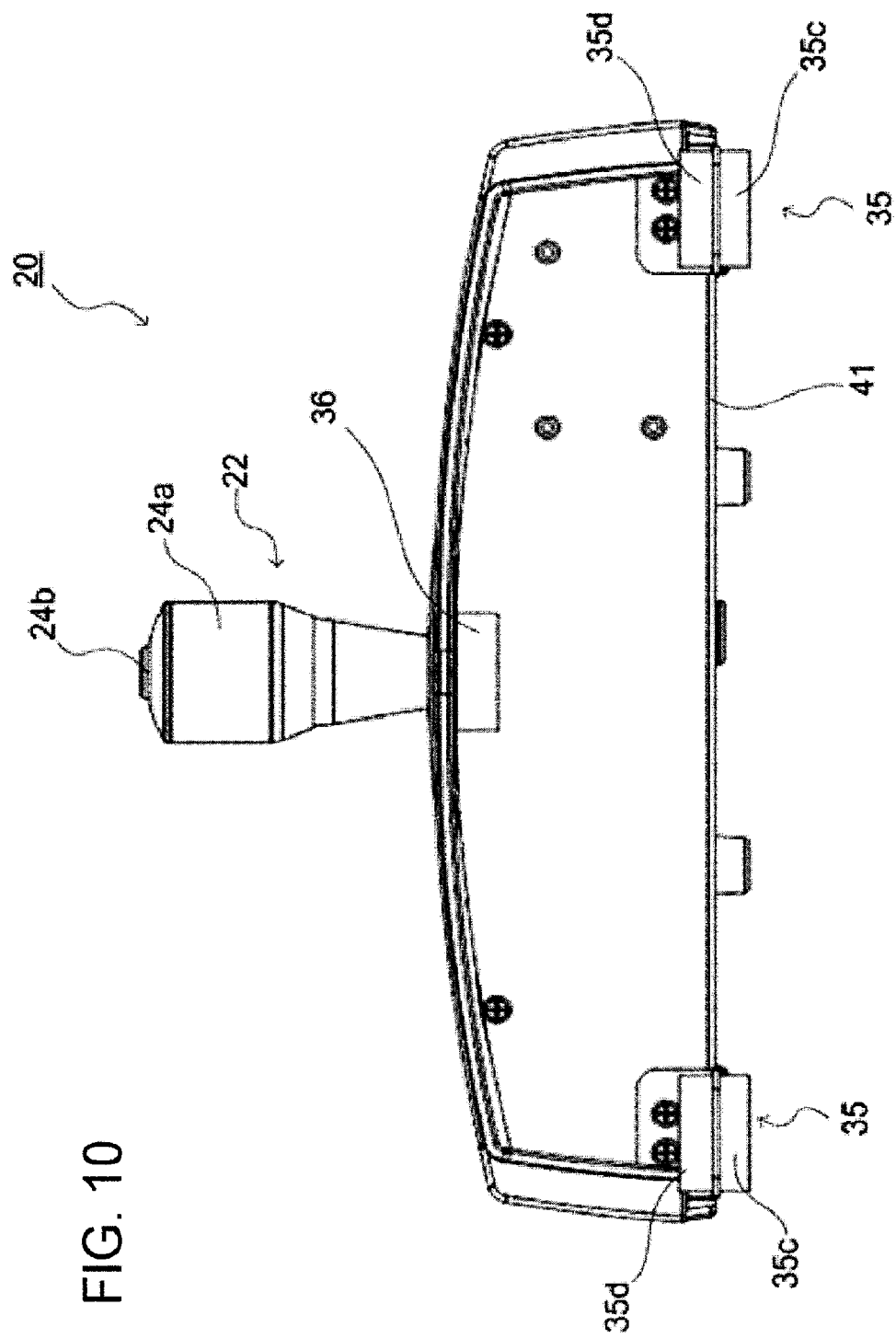
FIG. 10 is a schematic diagram illustrating an example of the exterior configuration of the operation unit of the embodiment.

FIGS. 6 to 10 are schematic diagrams illustrating the exterior configuration of the operation unit 20 according to the embodiment. FIG. 6 is a perspective view of the operation unit 20. FIG. 7A is a plan view of the operation unit 20. FIG. 7B is a plan view of the operation unit 20 illustrated in FIG. 7A from which a control lever 22 is removed. FIG. 8 is a front view of the operation unit 20. FIG. 9 is a left side view of the operation unit 20. FIG. 10 is a rear view of the operation unit 20. In FIGS. 6 to 10, like reference numerals designate like parts, and the same description may not be repeated.

Figure 11:
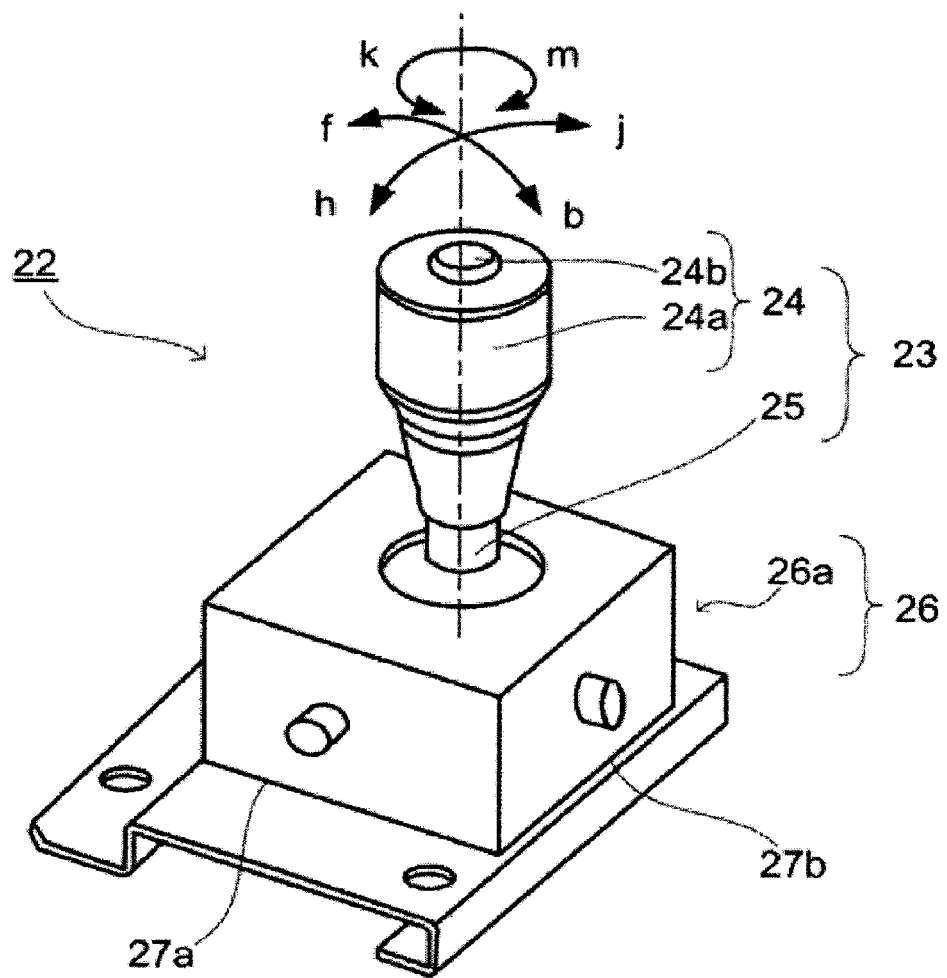
FIG. 11 is a schematic diagram illustrating an example of the exterior configuration of a control lever of the embodiment.

FIG. 11 is a perspective view illustrating the external configuration of the control lever 22 that constitutes the operation unit 20. In FIG. 11, like reference numerals designate like parts as in FIGS. 6 to 10, and the same description may not be repeated.

As illustrated in FIGS. 6 to 10, the operation unit 20 includes the control lever 22, a first switch 30, a second switch 31, and a lighting unit 32. The control lever 22 is configured to be tilted in any direction by operation. The first switch 30 is a switch member for sequentially switching a plurality of measurement modes of the ophthalmologic apparatus 1 in a predetermined order. The measurement modes are determined in advance. The second switch 31 is a switch member for switching the eye to be measured to the right eye or the left eye. The lighting unit 32 includes a light emitting element for indicating, by lighting or non-lighting, the presence or absence of power supply from the ophthalmologic apparatus 1 via the USB cable.

As illustrated in FIG. 11, the control lever 22 includes an operating lever 23, and a support portion 26. One end of the operating lever 23 (the proximal end or base end) is tiltably supported by the support portion 26. The operating lever 23 includes a grip 24 and a support shaft 25. The grip 24 is connected to the distal end of the support shaft 25. The proximal end of the support shaft 25 is connected to the support portion 26. The grip 24 includes an operation knob 24a configured to perform rotation operation, and a measurement switch 24b configured to perform press operation. The operation knob 24a is held rotatably about the support shaft 25. The measurement switch 24b is provided on the top of the grip 24.

The support portion 26 includes a mechanism 26a and a variety of detectors for detecting the tilting operation, rotating operation of the operating lever 23, and the like. The mechanism 26a includes a member for tilting the support shaft 25 in any direction from the proximal end of the support shaft 25 as a supporting point while supporting the proximal end. The detectors, for detecting the tilting operation, rotating operation of the operating lever 23, and the like, include a first potentiometer 27a, a second potentiometer 27b, a rotary encoder 27c (see FIG. 16), a switch operation detector 27d (see FIG. 16), and the like.

The first potentiometer 27a is coupled to a first rotation shaft for allowing the support shaft 25 to tilt forward and backward (in directions indicated by arrows f and b), and detects whether the tilt direction is forward or backward as well as the tilt angle. The second potentiometer 27b is coupled to a second rotation shaft for allowing the support shaft 25 to tilt leftward and rightward (in directions indicated by arrows h and j), and detects whether the tilt direction is leftward or rightward as well as the tilt angle. The rotary encoder 27c is coupled to a third rotation shaft for rotation centered on the support shaft 25 in rotation directions (directions indicated by arrows k and m), and detects whether the rotation direction is leftward or rightward as well as the rotation angle. The switch operation detector 27d detects the pressing of the measurement switch 24b. The control lever 22 (in particular, the mechanism 26a) has a known configuration as described in, for example, Japanese Unexamined Patent Application Publication No. 2008-61715. Accordingly, the configuration of the control lever 22 is not described in detail herein.

The operating lever 23 and at least part of the aforementioned detectors for detecting the operation of tilting or rotating the operating lever 23 are accommodated in a housing 40. In this embodiment, part of the control lever 22 (at least part of the support portion 26) is housed in the housing 40.

The housing 40 include, for example, a base 41 and a cover 42. The first switch 30, the second switch 31, and the lighting unit 32 are arranged on the upper surface of the cover 42. The mechanism 26a is fixed to the base 41. Thereby, at least part of the support portion 26 is housed in the housing 40. The cover 42 has an opening 42a formed therein. The operating lever 23 (the grip 24, the support shaft 25) is provided so as to protrude upward from the opening 42a. The housing 40 is provided with switch operation detectors 30a and 31a for detecting the pressing of the first switch 30 and the second switch 31 (see FIG. 16).

<Protrusion>

As illustrated in FIGS. 6 to 9, the cover 42 is provided with a protrusion 45. The protrusion 45 is provided around the periphery of the opening 42a so as to protrude upward. At least part of the housing 40 (the cover 42) and the protrusion 45 are formed integrally. In this embodiment, the protrusion 45 is provided over the entire circumference of the opening 42a. That is, the protrusion 45 is formed annularly to surround the opening 42a. With this, while performing operation on the operation unit 20 at any position as illustrated in FIG. 1A to FIG. 5B, the examiner can tilt and rotate the operating lever 23 by hooking the protrusion 45 with the bent little finger or the little finger ball of his/her hand used for manipulation. Thus, the operability can be improved.

Regarding the height of the protrusion 45 from the upper surface of the cover 42, the height of the lowest portion may be equal to or more than a first threshold th1 and equal to or less than a second threshold th2 (0<th1<th2) so that the examiner can easily operate the operation unit 20 in any position. In the embodiment, since the upper surface of the cover 42 is inclined such that it becomes lower toward the front from the rear, the rear portion of the protrusion 45 is the lowest and has a height H as illustrated in FIG. 9. The first threshold th1 is, for example, the minimum value of the height at which the little finger or the little finger ball of the hand used for manipulation can easily be hooked on the protrusion 45. The second threshold th2 is, for example, the minimum value of the height at which the examiner can tilt and rotate the operating lever 23 with no trouble while hooking the protrusion 45 with the little finger or the little finger ball of his/her hand used for manipulation. Specifically, the height of the lowest portion of the protrusion 45 may be 5 mm or more and 10 mm or less. As to the protrusion 45 of the embodiment, the height of the lowest portion is 7.5 mm or more and 8 mm or less. The height of the highest portion of the protrusion 45 is determined by, for example, the tilt angle range to be ensured.

The protrusion 45 may have an outer shape of a non-perfect circle as viewed from the above. This allows the examiner to hook the bent little finger or the little finger ball of his/her hand used for manipulation on the protrusion 45. In this embodiment, as illustrated in FIG. 7B, the protrusion 45 is provided to have an outer shape of an ellipse as viewed from the above. Here, the major diameter d1 in the lateral direction is greater than the minor diameter d2 in the front-back direction. Incidentally, in the embodiment, the outer shape of the protrusion 45 is not limited to that as viewed from the above; the protrusion 45 may have an outer shape of a perfect circle.

If the outer shape is a non-perfect circle as viewed from the above, the protrusion 45 may be configured to be rotatable around the axis passing through the opening 42a. That is, the protrusion 45 may be configured such that the orientation of its outer shape as viewed from the above is varied by the rotation thereof. In this case, the protrusion 45 is configured to be able to hold the position after the rotation. Accordingly, by rotating the protrusion 45 to easily operate the operating lever 23, the examiner can tilt and rotate it at any position with optimum operability. The protrusion 45 may also be configured to have a variable outer shape.

In this embodiment, although the protrusion 45 is described as being provided over the entire circumference of the opening 42a, it may be provided to a part of the periphery of the opening 42a. For example, the protrusion 45 may be provided only to the periphery of the back side of the opening 42a. Besides, a plurality of protrusions may be arranged around the periphery of the opening 42a.

<Connection Hook>

The back of the housing 40 (the operation unit 20) may have an outer shape that allows it to be arranged in proximity to the ophthalmologic apparatus 1. For example, the back of the housing 40 may be formed in a shape that extends along the surface of the housing of the ophthalmologic apparatus 1 when it is arranged facing the surface. As illustrated in FIGS. 6 to 10, one or more plate-shaped connection hooks 35 are fixed to the operation unit 20 so as to protrude from the back of the housing 40. In this embodiment, the two connection hooks 35 are attached to the rear side of the base 41 at positions apart by a predetermined distance in the lateral direction. Note that the attachment position of the connection hooks 35 relative to the base 41 in the embodiment is not limitation, and the number and shape of the connection hooks 35 are also not limitation.

In the following, the two connection hooks 35 provided on the operation unit 20 are described as having the same shape; however, their shapes may be different from each other. At least one of a plurality of connection hooks 35 provided on the operation unit 20 may be configured as follows.

The connection hooks 35 are used to physically fix the ophthalmologic apparatus 1 and the operation unit 20 so that they do not move when the operating lever 23 is tilted. In this embodiment, by applying the weight of the ophthalmologic apparatus 1 to the connection hooks 35, it is possible to restrict the movement of the operation unit 20 to which the connection hooks 35 are fixed. Further, by engaging the connection hooks 35 to the ophthalmologic apparatus 1, it is also possible to restrict the movement of the operation unit 20 to which the connection hooks 35 are fixed. In the following, a description is given of a case for restricting the movement of the operation unit 20 by the own weight of the ophthalmologic apparatus 1 and the engagement with the ophthalmologic apparatus 1. On the other hand, the movement of the operation unit 20 may be restricted by either the own weight of the ophthalmologic apparatus 1 or the engagement with the ophthalmologic apparatus 1.

The connection hooks 35 include, for example, a contact portion that is in contact with a portion of the bottom surface of the ophthalmologic apparatus 1 to which the operation unit 20 is attached. The contact portion is provided, for example, on the upper surface of the connection hooks 35. The bottom surface of the ophthalmologic apparatus 1 may be the bottom surface of the housing of the ophthalmologic apparatus 1, a leg protruding from the bottom surface downward (including side surfaces of the leg), or the bottom surface of the leg. When the upper surfaces of the connection hooks 35 come in contact with a portion of the bottom surface of the housing of the ophthalmologic apparatus 1 or the like, the weight of the ophthalmologic apparatus 1 is applied to the upper surface of the connection hooks 35. Thereby, the movement of the operation unit 20 is restricted.

The connection hooks 35 further include, for example, an engagement portion to be engaged with the ophthalmologic apparatus 1. The engagement portion can be engaged at any position of the ophthalmologic apparatus 1. In this embodiment, the engagement portion is engaged with the leg provided on the bottom surface of the ophthalmologic apparatus 1.

In the connection hooks 35, a through region that penetrates through the connection hooks 35 from the upper surface to the lower surface is formed. In this embodiment, the through region is a through hole 35a in which the leg projecting downwardly from the bottom surface of the housing of the ophthalmologic apparatus 1 is inserted. However, the through region is only required to be a region through which the leg projecting from the bottom surface of the ophthalmologic apparatus 1 can be inserted. The through region may be in a shape formed by cutting a part of the connection hooks 35. Examples of the shape of the through region include U-shape with the open distal end, C-shape with the open right end, inverted C-shape with the open left end, inverted J-shape opened on the front side, and the like.

At least part of the edge of the through region is covered with a cover 35b. The cover 35b serves as an edge protection member and prevents the scratching of the leg of the ophthalmologic apparatus 1 inserted into the through region. The cover 35b also serves as a leg holding member to hold the leg of the ophthalmologic apparatus 1 inserted into the through region, thereby restricting the movement of the operation unit 20.

The connection hooks 35 are provided with a slip stopper 35c on their lower surfaces. For example, a surface of the slip stopper 35c having a substantially rectangular parallelepiped shape is bonded to the lower surface of the end of the connection hook 35. The slip stopper 35c may be a member having elasticity. Examples of the slip stopper 35c include silicon rubber. As the lower surface (the surface opposite to the bonding surface) of the slip stopper 35c is in contact with the supporting surface of the operation unit 20, the movement of the operation unit 20 is restricted.

The connection hooks 35 are provided with a cushioning member 35d on their upper surfaces. For example, a surface of the cushioning member 35d having a substantially rectangular parallelepiped shape is bonded to the upper surface of the end of the connection hook 35. At least part of the bonding surface of the cushioning member 35d may be a surface opposite to the bonding surface of the slip stopper 35c via the connection hook 35. As the upper surface (the surface opposite to the bonding surface) of the cushioning member 35d is in contact with the bottom surface of the housing of the ophthalmologic apparatus 1, the ophthalmologic apparatus 1 and the operation unit 20 are protected.

Further, the housing 40 is provided with a cushioning member 36 on the surface facing the ophthalmologic apparatus 1 when attached to the ophthalmologic apparatus 1. For example, a surface of the cushioning member 36 having a substantially rectangular parallelepiped shape is bonded to the aforementioned surface of the housing 40. As the surface opposite to the bonding surface of the cushioning member 36 is in contact with the housing of the ophthalmologic apparatus 1 while the operation unit 20 is attached to the ophthalmologic apparatus 1, the ophthalmologic apparatus 1 and the operation unit 20 are protected.

<Ophthalmologic Apparatus System>

Figure 12:
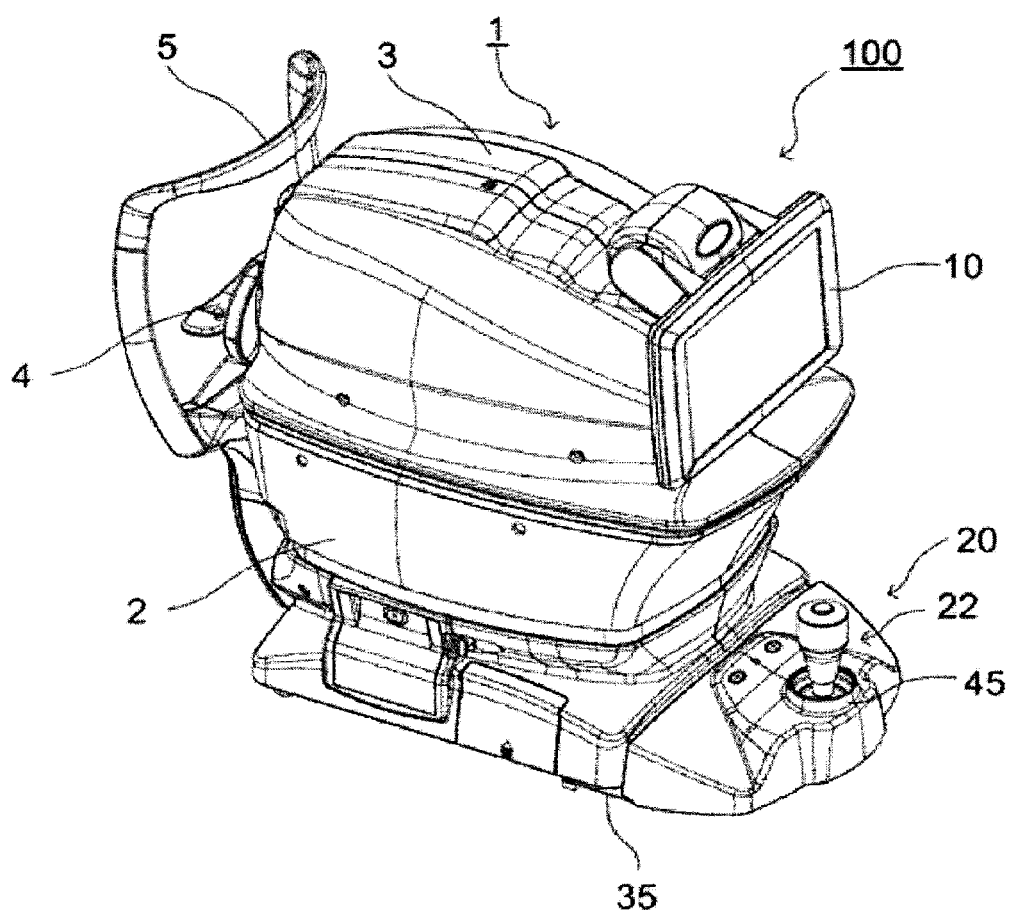
FIG. 12 is a schematic diagram illustrating an example of the exterior configuration of the ophthalmologic apparatus system of embodiment.
Figure 13:
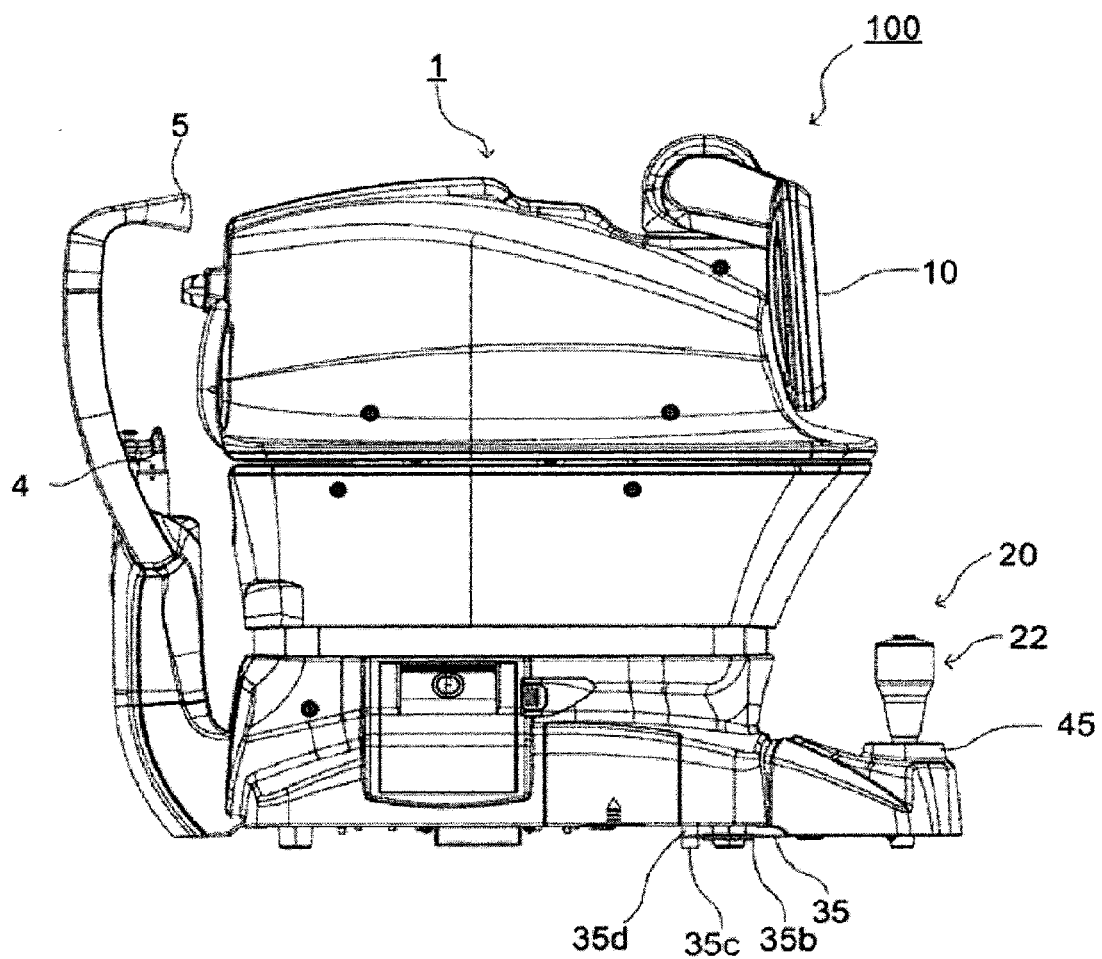
FIG. 13 is a schematic diagram illustrating an example of the exterior configuration of the ophthalmologic apparatus system of embodiment.

FIGS. 12 and 13 are schematic diagrams illustrating the exterior configuration of the ophthalmologic apparatus system of embodiment. FIG. 12 is a perspective view of the ophthalmologic apparatus system. FIG. 13 is a side view of the ophthalmologic apparatus system.

An ophthalmologic apparatus system 100 of the embodiment includes the ophthalmologic apparatus 1 and the operation unit 20 attached to the ophthalmologic apparatus 1. As described above, by inserting the leg of the ophthalmologic apparatus 1 in the through hole 35a formed in the connection hooks 35 provided on the operation unit 20, the weight of the ophthalmologic apparatus 1 is applied to the connection hooks 35. Accordingly, the movement of the operation unit 20 is restricted during operation. Thus, the examiner can operates the operation unit 20 at any position as illustrated in FIGS. 1A to 5B. In this case, fine adjustment can be made without lowering the operability by tilting operation similar to the conventional manner. Besides, since the operation unit 20 can be arranged close to the ophthalmologic apparatus 1, it is possible to save space for the arrangement of equipment that allows the tilting operation at any position without impairing the operability.

<Cable Connection>

As described above, the ophthalmologic apparatus 1 and the operation unit 20 are connected by a USB cable. By connecting the ophthalmologic apparatus 1 and the operation unit 20 with the USB cable by the following manner, the cabling can be reduced. Further, it also becomes possible to improve the safety at the time of examination such that the examiner, the examinee, and the like are not likely to be caught by the USB cable.

Figure 14:
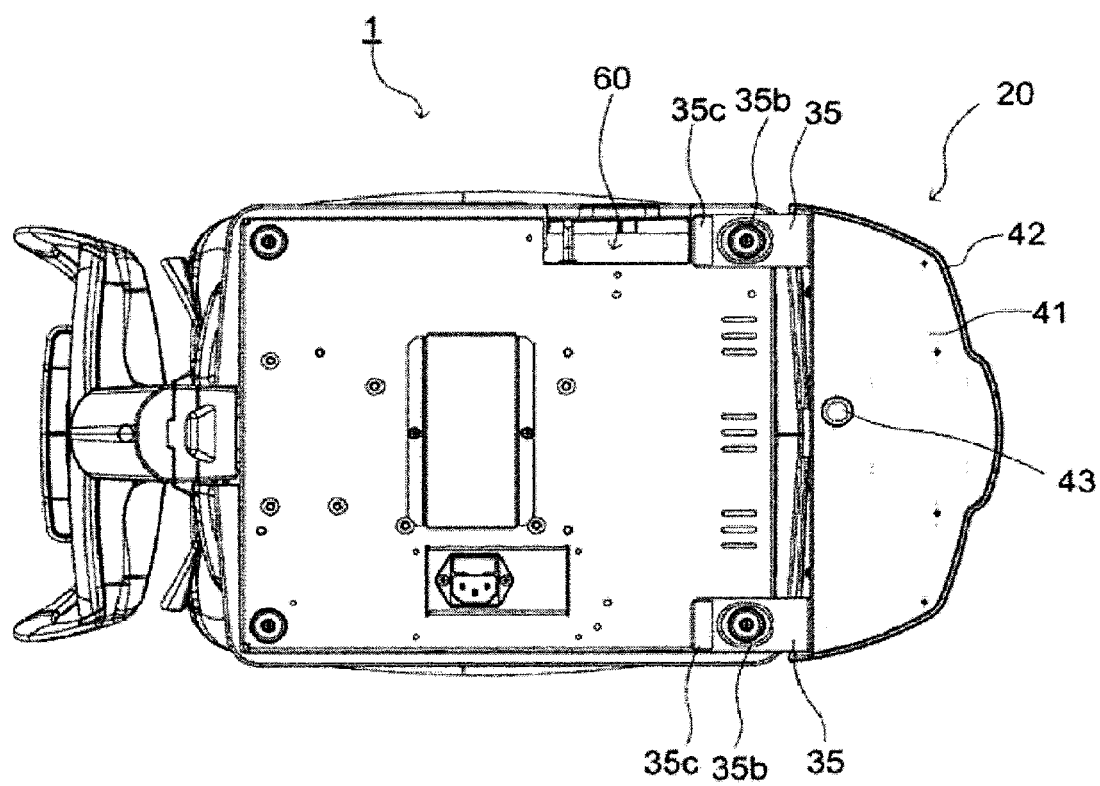
FIG. 14 is an explanatory diagram illustrating the wiring of USB cable in the ophthalmologic apparatus system of the embodiment.
Figure 15A:
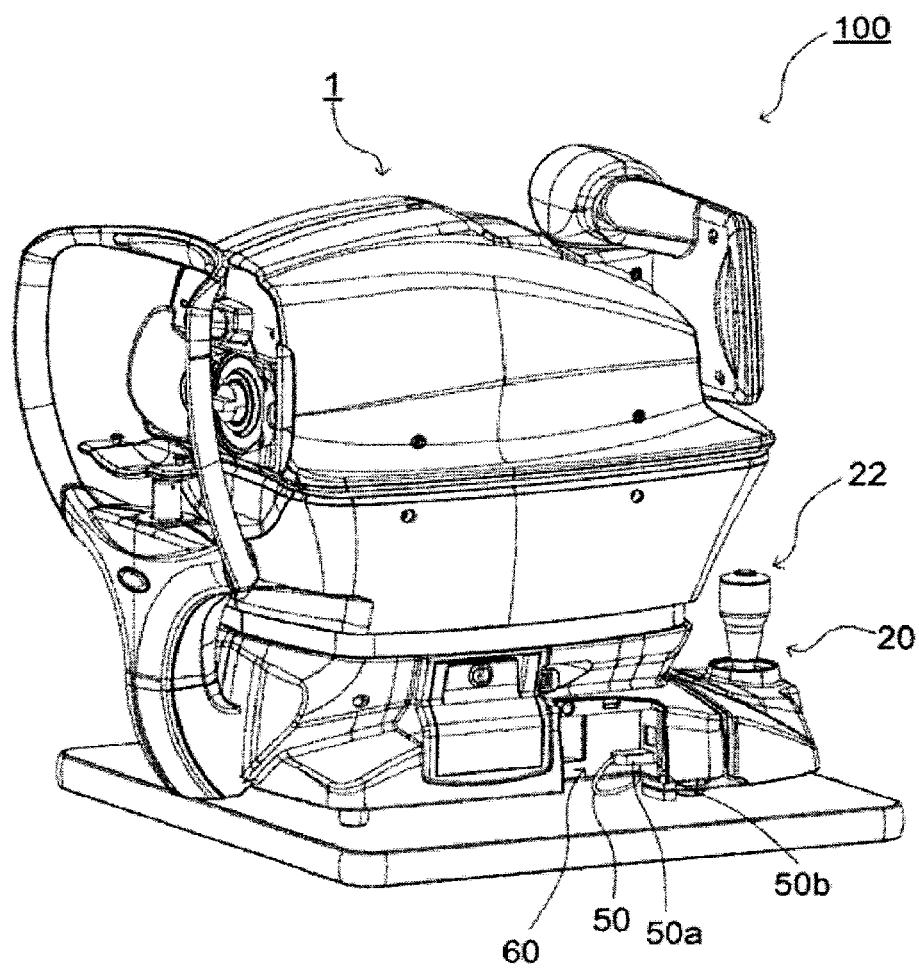
FIG. 15A is an explanatory diagram illustrating the wiring of USB cable in the ophthalmologic apparatus system of the embodiment.
Figure 15B:
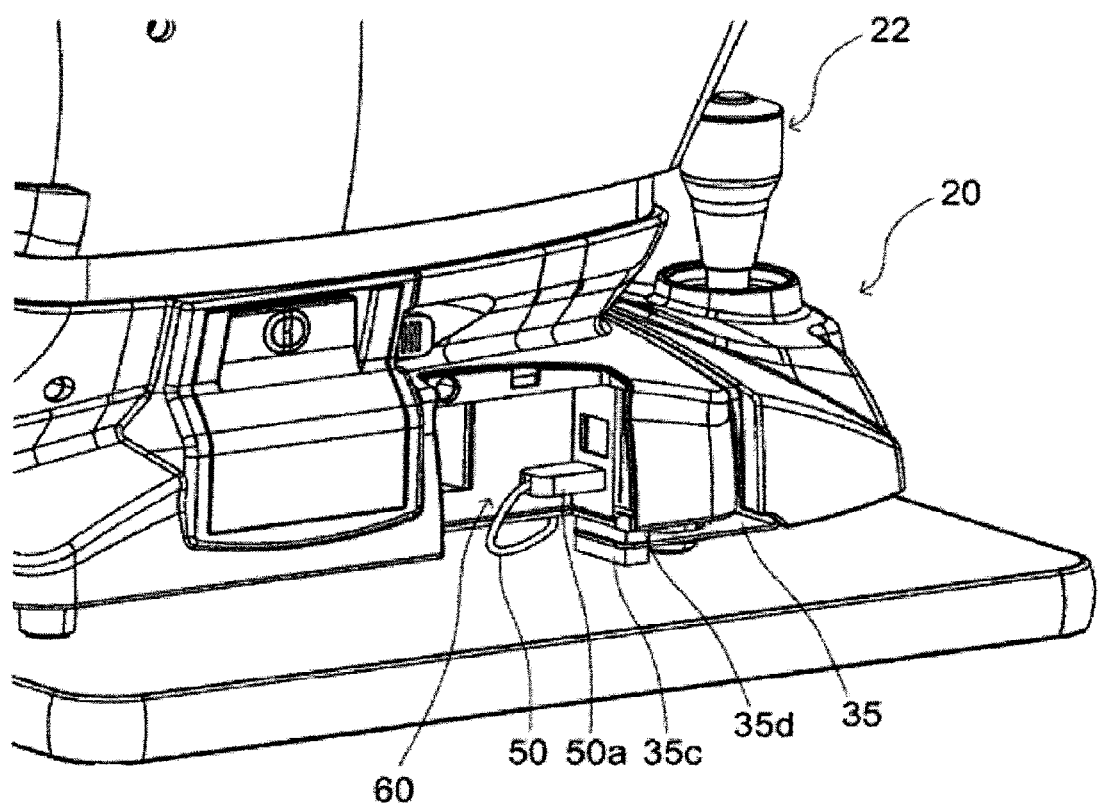
FIG. 15B is an explanatory diagram illustrating the wiring of USB cable in the ophthalmologic apparatus system of the embodiment.
Figure 15C:
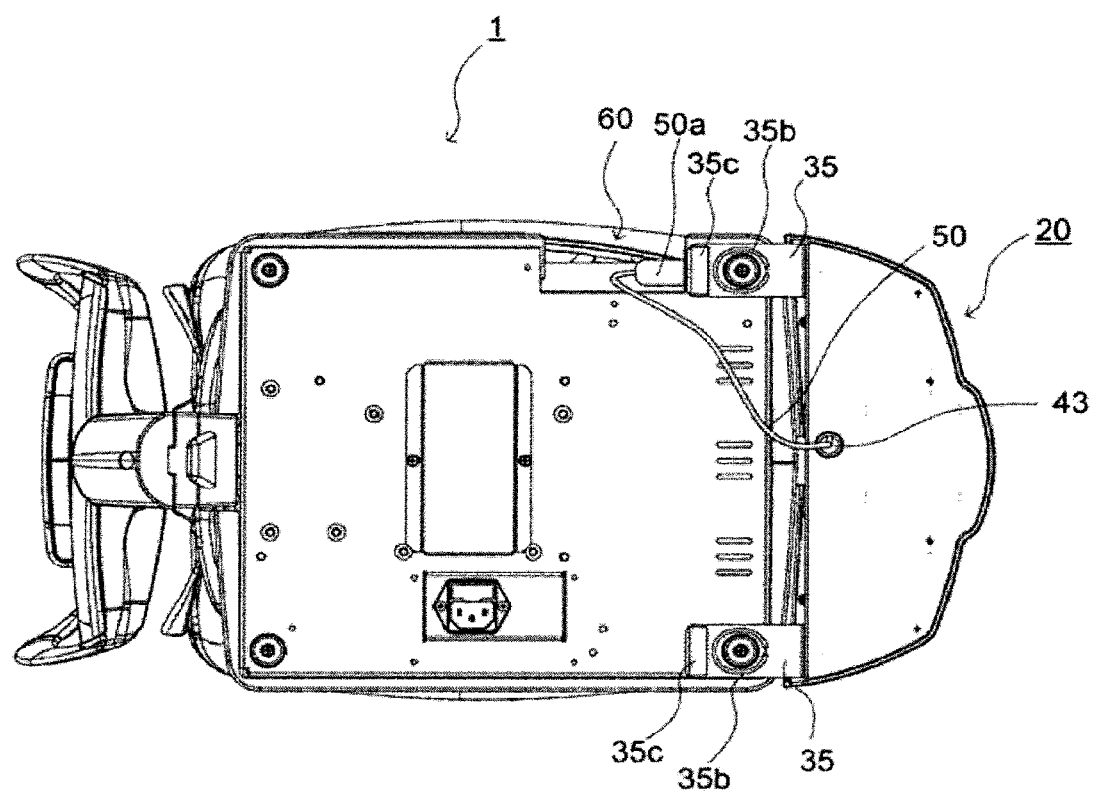
FIG. 15C is an explanatory diagram illustrating the wiring of USB cable in the ophthalmologic apparatus system of the embodiment.
Figure 15D:
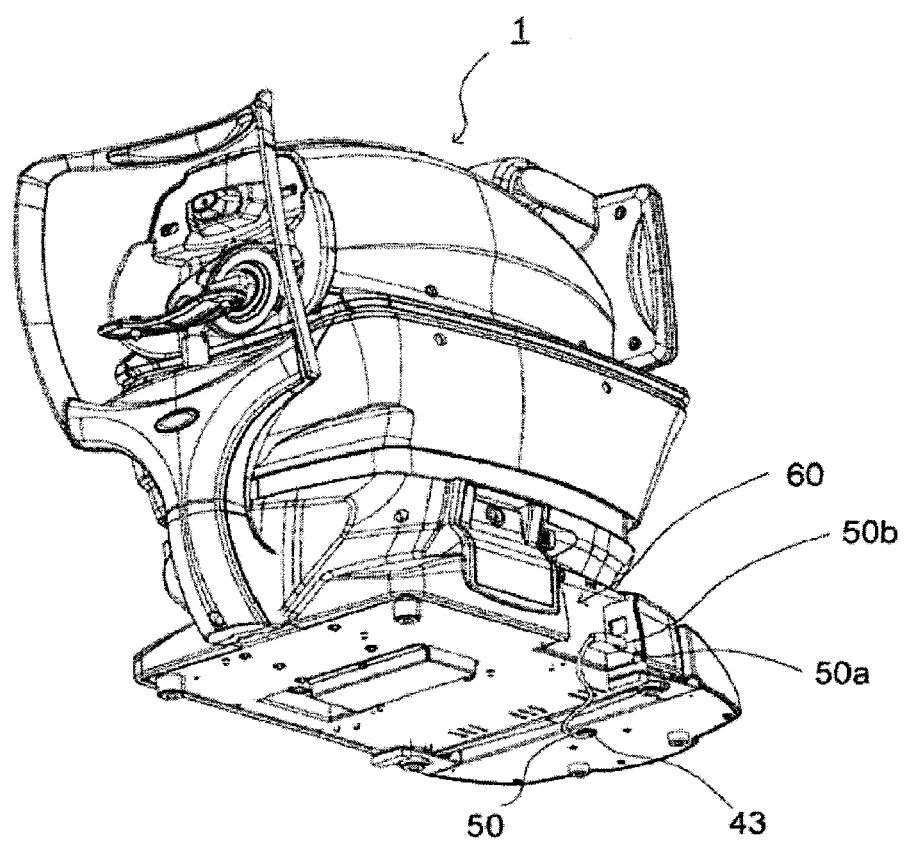
FIG. 15D is an explanatory diagram illustrating the wiring of USB cable in the ophthalmologic apparatus system of the embodiment.
Figure 15E:
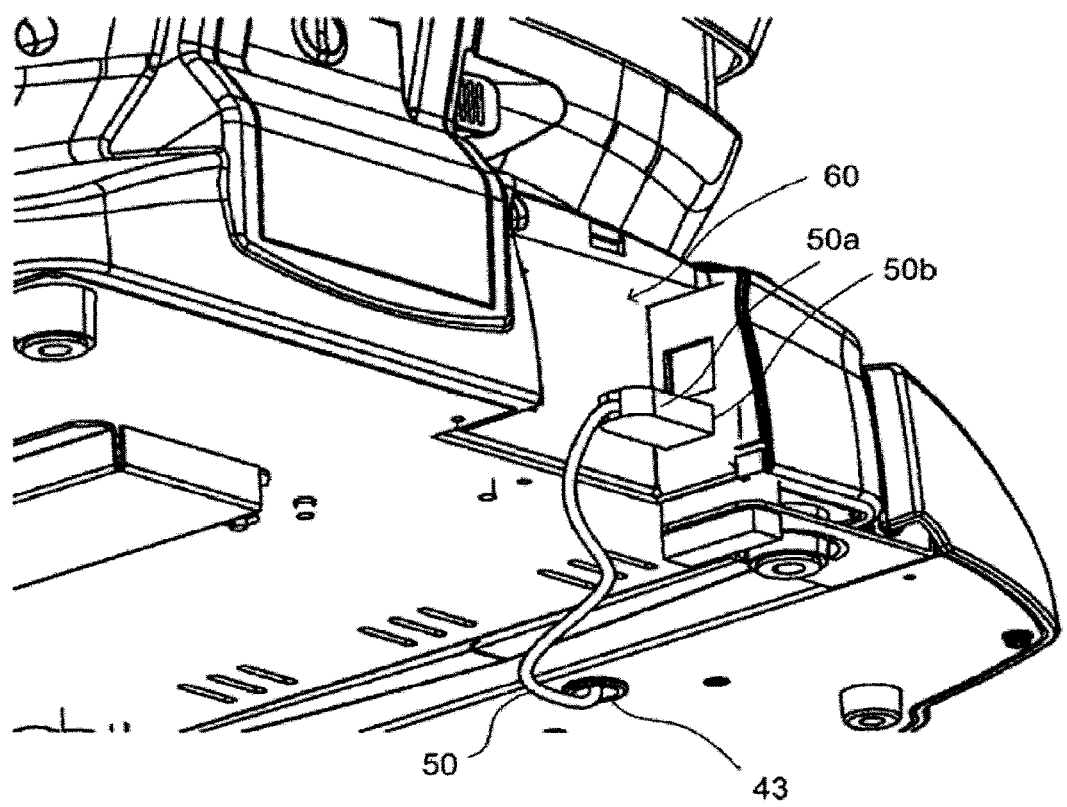
FIG. 15E is an explanatory diagram illustrating the wiring of USB cable in the ophthalmologic apparatus system of the embodiment.

FIGS. 14 and 15A to 15E are explanatory views illustrating the connection status of the USB cable in the ophthalmologic apparatus system 100 of the embodiment. FIG. 14 is a bottom view of the ophthalmologic apparatus system 100. FIG. 15A is a perspective view of the ophthalmologic apparatus system 100. FIG. 15B is an enlarged view around a cable connection portion 60 of FIG. 15A. FIG. 15C is a bottom view of the ophthalmologic apparatus system 100 for explaining the wiring of the USB cable. FIG. 15D is a perspective view of the ophthalmologic apparatus system 100 in which the ophthalmologic apparatus 1 and the operation unit 20 are connected by a USB cable. FIG. 15E is an enlarged view around the cable connection portion 60 of FIG. 15D. In FIGS. 14 and 15A to 15E, like reference numerals designate like parts, and the same description may not be repeated.

In the lower surface of the housing 40 (the base 41) of the operation unit 20, a through hole 43 is formed so that one end of a USB cable 50 can be drawn out of the housing 40 to the outside (see, for example, FIG. 14). The other end of the USB cable 50 is provided with a USB connector (plug) 50a.

The height of the leg provided on the bottom surface of the housing of the ophthalmologic apparatus 1 is greater than the thickness of a USB connector 50a. The leg is provided so as to protrude downward from the bottom surface of the housing 40 of the operation unit 20, and the height of the leg is greater than the thickness of the USB connector 50a. Thereby, the USB cable 50 can be routed arbitrarily in a lower space formed below the bottom surface of the housing of the ophthalmologic apparatus 1 and the bottom surface of the housing 40 of the operation unit 20.

The cable connection portion 60 is located below the side face of the ophthalmologic apparatus 1. The cable connection portion 60 is provided in a recess formed by cutting the side surface of the housing of the ophthalmologic apparatus 1 to the bottom. The recess is provided with one or more USB connectors (receptacle) 50b on its side surface. The USB connector 50b is provided to be inserted in a direction toward the operation unit 20. The side and upper surfaces of the cable connection portion 60, which are formed in a recessed shape, can be covered by a removable cover. There is an opening below the recess space of the cable connection portion 60 formed by a cutout as described above. Thereby, the recess space is communicated with the lower space formed below the bottom surface of the housing of the ophthalmologic apparatus 1. The USB cable 50 is wired to pass through the opening below the recess space from the lower space beneath the bottom surface of the housing of the ophthalmologic apparatus 1 (FIGS. 15A to 15E). As the USB connector 50a is inserted into the USB connector 50b in the recess space of the cable connection portion 60, the USB connection is established between the ophthalmologic apparatus 1 and the operation unit 20. Between the ophthalmologic apparatus 1 and the operation unit 20 connected by the USB, signals are transmitted and received in conformity with the USB standard.

The connection hooks 35 are an example of the "connection member" of the embodiment. The control lever 22, the first potentiometer 27a, the second potentiometer 27b, the rotary encoder 27c, the first switch 30, the second switch 31, the switch operation detectors 27d, 30a, and 31a are examples of the "operation unit" of the embodiment.

<Control System>

FIG. 16 illustrates an example of the configuration of a control system of the ophthalmologic apparatus system 100. In FIG. 16, like reference numerals designate like parts as in FIGS. 1A to 15E, and the same description may not be repeated.

A controller 200 is the center of the control system of the ophthalmologic apparatus system 100. The controller 200 includes, for example, a microprocessor, a random access memory (RAM), a read only memory (ROM), a hard disk drive, and the like. The controller 200 includes a main controller 201 and a storage 202.

The main controller 201 controls each unit of the ophthalmologic apparatus 1. In particular, the main controller 201 controls the measuring head 3, the drive unit 8, the UI 10, a communication interface 210. As the control for the measuring head 3, for example, the main controller 201 controls an optical system for measuring the characteristics of the subject's eye or photographing the subject's eye. As the control for the drive unit 8, for example, the main controller 201 controls driving of an up-and-down drive motor 8a, a side-to-side drive motor 8b, and a back-and-forth drive motor 8c. As the control for the UI 10, for example, the main controller 201 controls the display of the operation screen as well as an image of the subject's eye obtained using the measuring head 3, and receipt of touch operation on the UI 10. As the control for the communication interface 210, for example, the main controller 201 controls receipt of various operations, such as tilting operation on the operation unit 20. The main controller 201 controls each unit of the ophthalmologic apparatus 1 based on the operation made on the UI 10 or the operation unit 20.

The operation unit 20 includes the operating lever 23, the first potentiometer 27a, the second potentiometer 27b, the rotary encoder 27c, the switch operation detector 27d, and a communication interface 29. The communication interface 29 provides an interface to the communication interface 210. The operation unit 20 includes the first switch 30, the second switch 31, and the switch operation detectors 30a and 31a. The switch operation detector 30a detects the pressing of the first switch 30. The switch operation detector 31a detects the pressing of the second switch 31.

An operation detection signal corresponding to the tilt direction and the tilt angle detected by the first potentiometer 27a is sent from the communication interface 29 to the ophthalmologic apparatus 1. An operation detection signal corresponding to the tilt direction and the tilt angle detected by the second potentiometer 27b is sent from the communication interface 29 to the ophthalmologic apparatus 1. An operation detection signal corresponding to the rotation direction and the rotation angle detected by the rotary encoder 27c is sent from the communication interface 29 to the ophthalmologic apparatus 1. An operation detection signal corresponding to the operation performed on the measurement switch 24b detected by the switch operation detector 27d is sent from the communication interface 210 to the ophthalmologic apparatus 1. An operation detection signal corresponding to the operation performed on the first switch 30 detected by the switch operation detector 30a is sent from the communication interface 210 to the ophthalmologic apparatus 1. An operation detection signal corresponding to the operation performed on the second switch 31 detected by the switch operation detector 31a is sent from the communication interface 210 to the ophthalmologic apparatus 1.

Under the control of the main controller 201, the communication interface 210 receives an operation detection signal, which corresponds to the operation performed on the operation unit 20, from the communication interface 29. The communication interface 210 is capable of detecting the connection with the communication interface 29 via a USB cable. Having detected the connection, the communication interface 210 notifies the main controller 201 of it. Having been notified of this information, the main controller 201 controls the communication interface 210 to thereby receive the operation detection signal corresponding to the operation performed on the operation unit 20 from the communication interface 29. With this, the main controller 201 can control each unit of the ophthalmologic apparatus 1 based on the operation performed on the operation unit 20. The function of the communication interface 210 may be implemented by the main controller 201.

The main controller 201 controls the back-and-forth drive motor 8c based on the operation detection signal corresponding to the detection result of the first potentiometer 27a. As a result, the measuring head 3 is moved in the back-and-forth direction. The main controller 201 controls the side-to-side drive motor 8b based on the operation detection signal corresponding to the detection result of the second potentiometer 27b. As a result, the measuring head 3 is moved in the lateral direction. The main controller 201 controls the up-and-down drive motor 8a based on the operation detection signal corresponding to the detection result of the rotary encoder 27c. As a result, the measuring head 3 is moved in the vertical direction.

The main controller 201 starts measurement by the measuring head 3 based on the operation detection signal corresponding to the detection result of the switch operation detector 27d. As a result, the measurement is performed in a sequence corresponding to the measurement mode which is currently set.

Based on the operation detection signal corresponding to the detection result of the switch operation detector 30a, the main controller 201 sequentially switches a plurality of measurement modes in a predetermined order. In this embodiment, the measurement modes include REF/KRT measurement mode and TONO/PACHO measurement mode. Each time the depression of the first switch 30 is detected by the switch operation detector 30a, the measurement modes are alternately switched between the REF/KRT measurement mode and the TONO/PACHO measurement mode. The REF/KRT measurement mode further includes refractometry measurement mode, keratometry measurement mode, and refraction/keratometry measurement mode, and measurement can be conducted in one of them. The refractometry measurement mode is a mode for measuring the sphere power, the cylinder power, and the astigmatic axial direction. The keratometry measurement mode is a mode for measuring the corneal curvature radius, the corneal astigmatism axis direction, and the corneal refractive power. The refraction/keratometry measurement mode is a mode for sequentially perform refractometry measurement and keratometry measurement. The TONO/PACHO measurement mode further includes TONO measurement mode and PACHO measurement mode, and measurement can be conducted in one of them. The TONO measurement mode is a mode for measuring the intraocular pressure. The PACHO measurement mode is a mode for measuring the intraocular pressure and the corneal thickness.

The main controller 201 moves the measuring head 3 to an examination position for the right eye or the left eye based on the operation detection signal corresponding to the detection result of the switch operation detector 31a. In this embodiment, each time the depression of the second switch 31 is detected by the switch operation detector 31a, the measuring head 3 is moved alternately between a predetermined examination position for the right eye and a predetermined examination position for the left eye.

The main controller 201 performs the process of writing data to the storage 202, and the process of reading data from the storage 202.

The storage 202 stores various types of data. Examples of the data stored in the storage 202 include image data of the subject's eye, subject's eye information, and the like. The subject's eye information includes information related to a subject such as a patient ID and name, and information related to the subject's eye such as the identification information of the left eye/right eye. The storage 202 further stores data and a variety of programs for operating the ophthalmologic apparatus 1.

Figure 17:
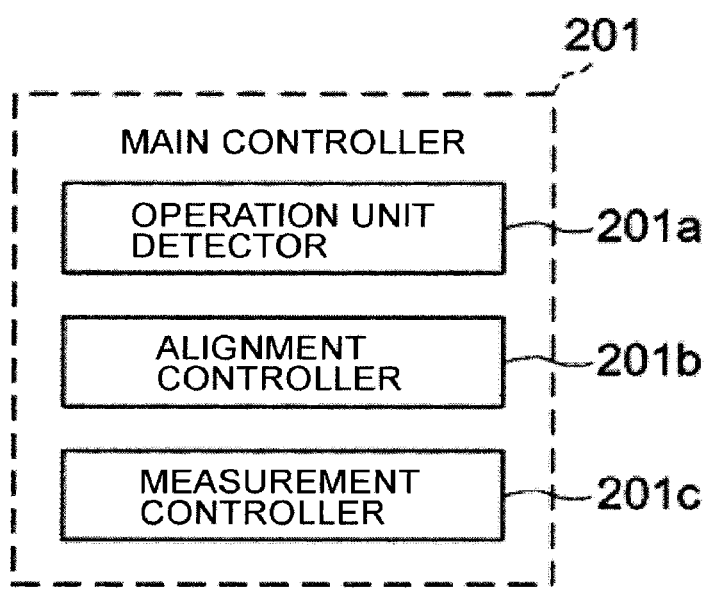
FIG. 17 is a schematic diagram illustrating an example of the configuration of a control system in the ophthalmologic apparatus system of the embodiment.

FIG. 17 is a block diagram illustrating an example of the configuration of the main controller 201. The main controller 201 includes an operation unit detector 201a, an alignment controller 201b, and a measurement controller 201c.

The operation unit detector 201a detects whether the operation on the operation unit 20 is enabled. The operation on the operation unit 20 can be regarded as enable when, for example, the ophthalmologic apparatus 1 can be operated using the operation unit 20 instead of the UI 10, or the ophthalmologic apparatus 1 can be operated using the operation unit 20 in addition to the UI 10. While the operation on the operation unit 20 is enabled, for example, the same operation as performed on the UI 10 can be performed by using the operation unit 20.

The operation on the operation unit 20 can be "enabled/disabled" by the connection/disconnection of the USB cable 50, power on/off of the operation unit 20 being connected by the USB cable 50. Alternatively, the operation may also be enabled/disabled by turning on/off the operation mode for receiving an operation detection signal from the operation unit 20.

If the operation on the operation unit 20 is enabled when the USB cable 50 is connected thereto, the operation unit detector 201a detects whether the USB cable 50 is connected to the ophthalmologic apparatus 1, thereby detecting whether the operation on the operation unit 20 is enabled or not. The communication interface 210 detects whether the USB cable 50 is connected to the USB connector 50b by a predetermined protocol conforming to the USB standard. The operation unit detector 201a is capable of detecting whether the USB cable 50 of the operation unit 20 is connected to the USB connector 50b by controlling the communication interface 210.

If the operation on the operation unit 20 becomes enabled by performing a predetermined operation such as switch operation while the USB cable 50 is being connected thereto, the operation unit detector 201a detects whether the predetermined operation has been performed. Examples of the predetermined operation include power-on of the operation unit 20, switching to the operation mode for receiving an operation detection signal from the operation unit 20, and the like. With this, the operation unit detector 201a can detect whether the operation on the operation unit 20 is enabled.

The alignment controller 201b controls the alignment unit provided to the measuring head 3 to thereby align the optical system with respect to the subject's eye. For example, the measuring head 3 includes, as the alignment unit, a Z alignment projection system for alignment in the Z direction, an XY alignment spot projection system for alignment in the XY direction.

The Z-alignment projection system includes, for example, a light source and a detector element. The light source projects light onto the cornea of the subject's eye. The detector element detects the light having projected onto the cornea by the light source and returning therefrom. The position of the return light projected onto the detector element changes as the position of the corneal apex is moved in the Z direction. To automatically perform the Z direction alignment, for example, the alignment controller 201b analyzes a change in the position of the return light detected on the detector element to obtain the position of the corneal apex of the subject's eye relative to the objective lens, and moves the measuring head 3 in the Z direction based on the position thus obtained.

The XY alignment spot projection system includes, for example, a light source. The optical path of light from the light source is combined with the optical path of the observation and imaging optical system 6. For example, light from the light source passes though the optical path of the observation and imaging optical system 6 and projected onto the cornea of the subject's eye. The light projected onto the subject's eye is reflected by the cornea, and is projected on an image pickup element provided separately for photographing. When alignment is automatically performed in the XY direction, for example, the alignment controller 201b moves the measuring head 3 in at least one of the X direction and the Y direction so as to cancel the deviation amount between a predetermined alignment target position and the position of return light projected onto the image pickup element.

The alignment controller 201b may perform the alignment of the measuring head 3 in any of a plurality of alignment modes. Examples of the alignment modes include automatic mode, manual mode, and semi-automatic mode. The automatic mode is a mode for automatically aligning the measuring head 3 with respect to the subject's eye as described above. The manual mode is a mode for manually aligning the measuring head 3 using the UI 10 or the operation unit 20. The semi-automatic mode is a mode in which the alignment mode is switched to the automatic alignment when an error in the alignment using the UI 10 or the operation unit 20 becomes within a predetermined range.

The alignment unit has a known configuration and the alignment controller 201b performs known control operation as described in, for example, Japanese Unexamined Patent Application Publication No. 2009-66025. Accordingly, the description is not provided herein.

The measurement controller 201c controls the measuring head 3 in the operation mode corresponding to the attachment state of the operation unit 20 detected by the operation unit detector 201a. For example, the measurement controller 201c uses different operation modes for enabled state in which the operation on the operation unit 20 is enabled and disabled state in which the operation on the operation unit 20 is disabled for performing display control of at least the UI 10. As an example, the measurement controller 201c displays, on the UI 10, different messages in the enabled state and the disabled state. The operation mode includes, for example, the alignment modes described above.

The measurement controller 201c can switch the operation mode to be employed after a transition to the enabled state according to the operation mode used in the ophthalmologic apparatus 1 (the measuring head 3) at the time of detecting the transition. For example, if a transition to the enabled state is detected while the automatic mode is being used, the measurement controller 201c controls the measuring head 3 in the automatic mode or the semi-automatic mode. On the other hand, if a transition to the enabled state is detected while the manual mode is being used, the measurement controller 201c controls the measuring head 3 in the manual mode.

<Example of Operation>

Figure 18A:
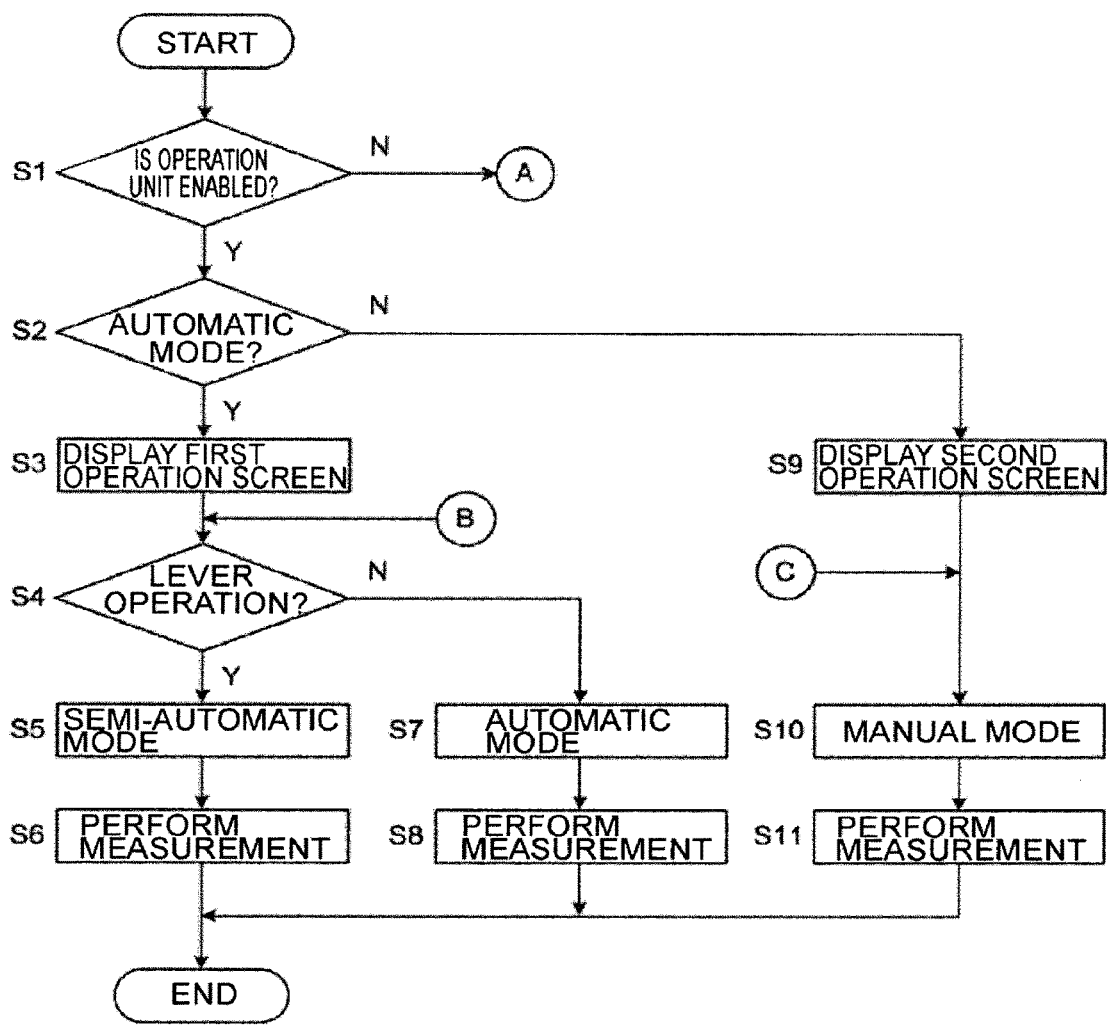
FIG. 18A is a flowchart illustrating an example of the operation of the ophthalmologic apparatus of the embodiment.
Figure 18B:
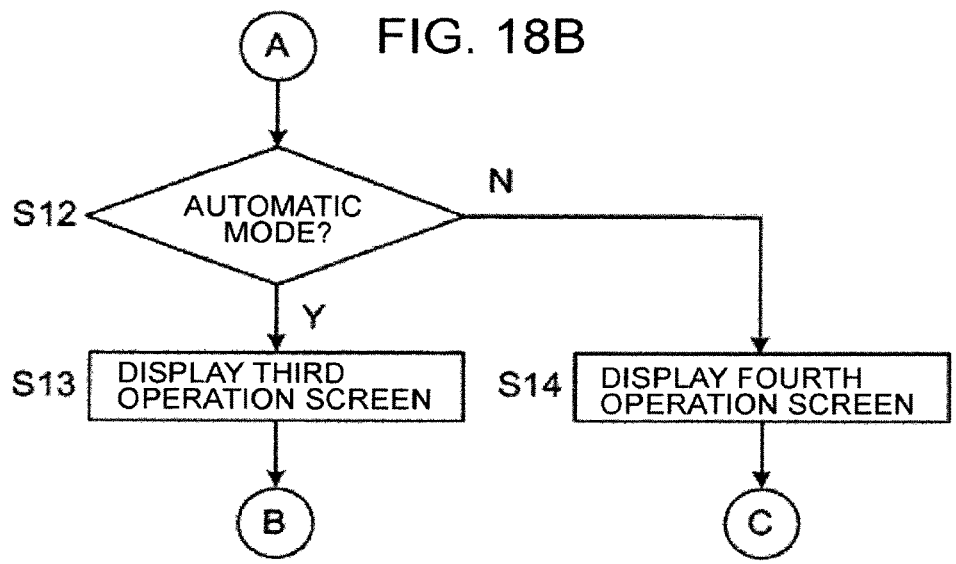
FIG. 18B is a flowchart illustrating an example of the operation of the ophthalmologic apparatus of the embodiment.

FIGS. 18A and 18B are flowcharts illustrating an example of the operation of the ophthalmologic apparatus of the embodiment. For example, the storage 202 stores, in advance, a program corresponding to the process illustrated in FIGS. 18A and 18B. The main controller 201 reads the program out of the storage 202, and performs the process corresponding to the program.

Figure 19A:
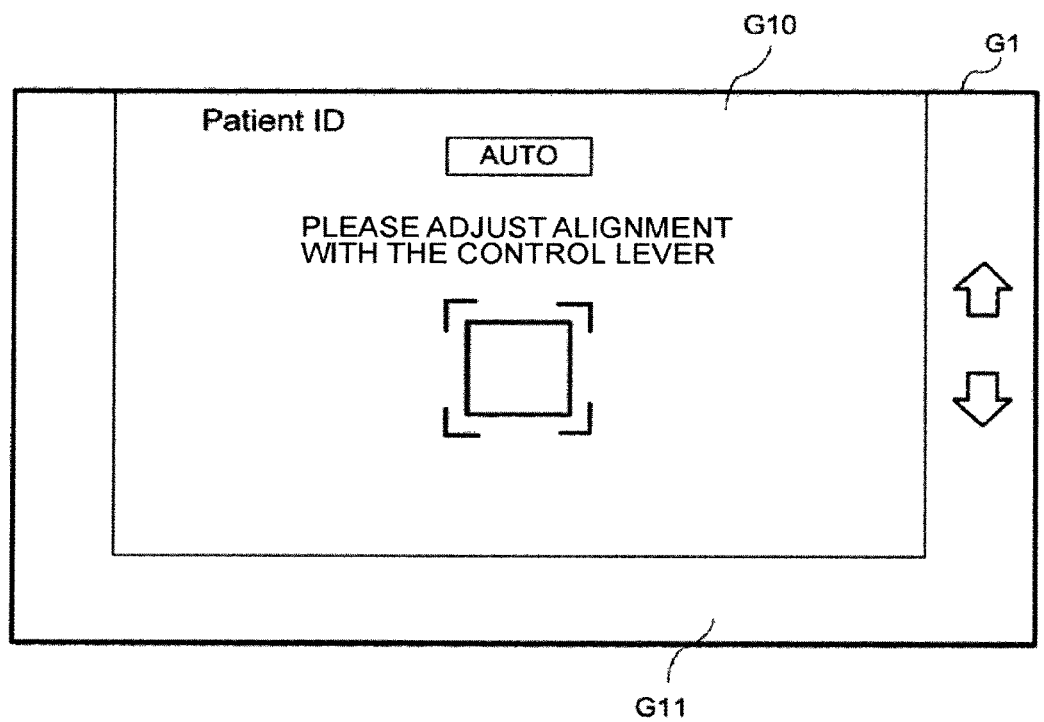
FIG. 19A is an explanatory diagram illustrating the operation of the ophthalmologic apparatus of the embodiment.
Figure 19B:
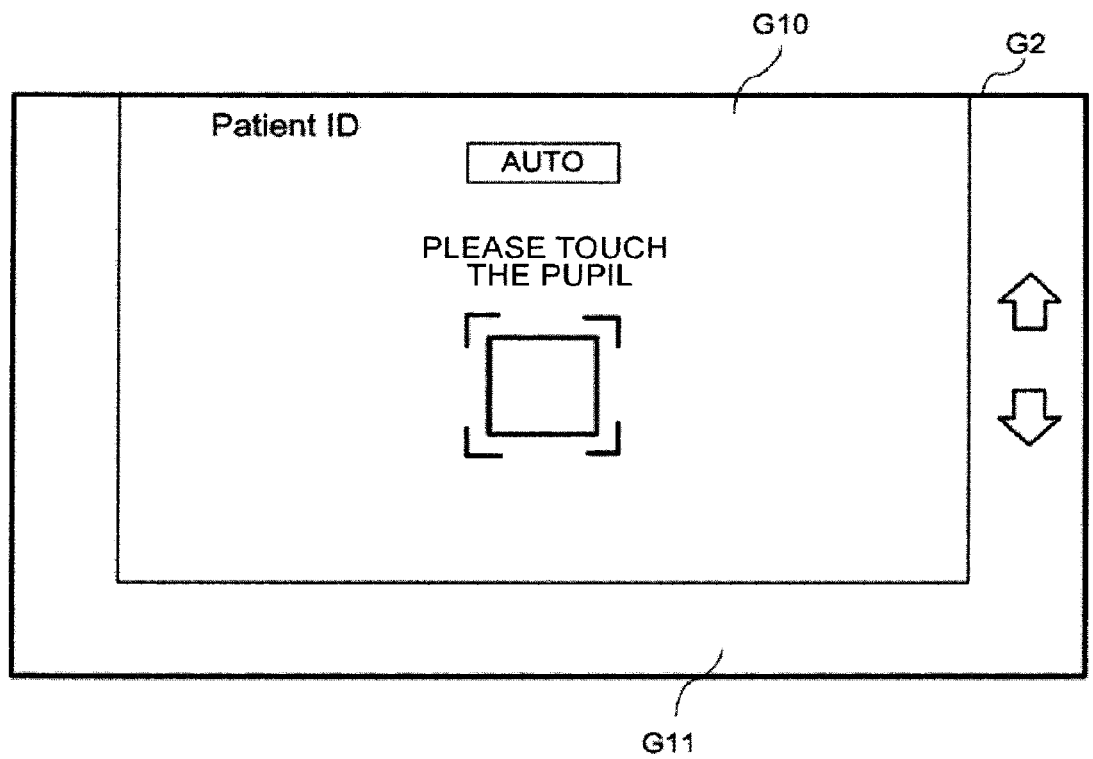
FIG. 19B is an explanatory diagram illustrating the operation of the ophthalmologic apparatus of the embodiment.
Figure 20A:
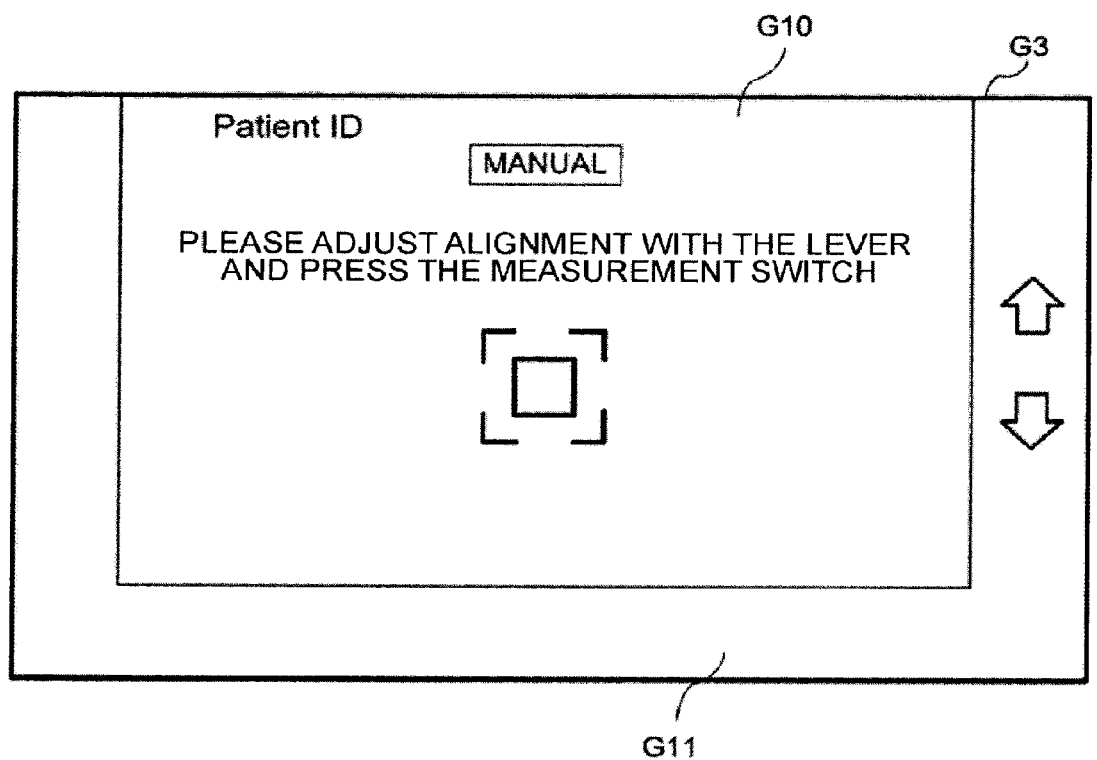
FIG. 20A is an explanatory diagram illustrating the operation of the ophthalmologic apparatus of the embodiment.
Figure 20B:
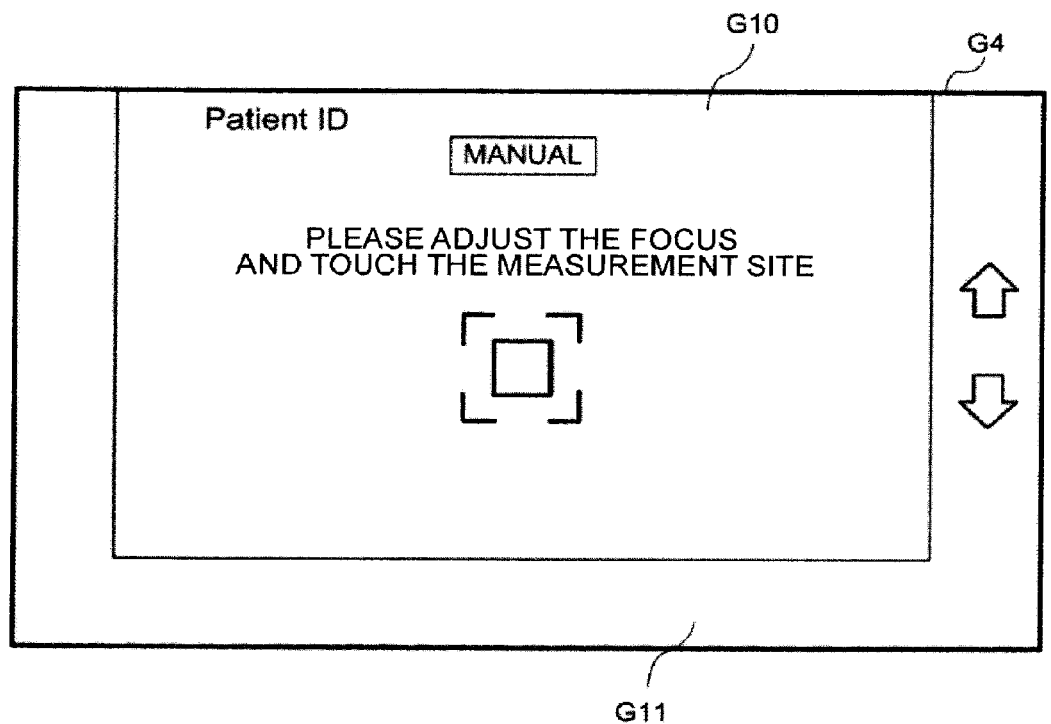
FIG. 20B is an explanatory diagram illustrating the operation of the ophthalmologic apparatus of the embodiment.

FIGS. 19A, 19B, 20A and 20B are explanatory diagrams for explaining the operation illustrated in FIGS. 18A and 18B. FIG. 19A illustrates an example of the operation screen displayed on the UI 10 when the operation on the operation unit 20 is disabled in the automatic mode. FIG. 19B illustrates an example of the operation screen displayed on the UI 10 when it is detected that the operation on the operation unit 20 is enabled in the automatic mode. FIG. 20A illustrates an example of the operation screen displayed on the UI 10 when the operation on the operation unit 20 is disabled in the manual mode. FIG. 20B illustrates an example of the operation screen displayed on the UI 10 when it is detected that the operation on the operation unit 20 is enabled in the manual mode. In FIGS. 19A, 19B, 20A, and 20B, like reference numerals designate like parts, and the same description may not be repeated.

(Step S1)

The operation unit detector 201a detects whether the operation on the operation unit 20 is enabled. When it is detected that the operation on the operation unit 20 is enabled (Y in step S1), the process proceeds to step S2. On the other hand, when it is detected that the operation on the operation unit 20 is disabled (N in step S1), the process proceeds to step S12.

(Step S2)

When it is detected that the operation on the operation unit 20 is enabled in step S1 (Y in step S1), the measurement controller 201c judges whether the alignment mode (operation mode) that is currently used is the automatic mode. When it is judged that the automatic mode is currently applied (Y in step S2), the process proceeds to step S3. On the other hand, when it is judged that the alignment mode that is currently applied is not the automatic mode (N in step S2), the process proceeds to step S9.

(Step S3)

When it is judged that the automatic mode is currently applied in step S2 (Y in step S2), the measurement controller 201c displays, on the UI 10, an operation window G1 as illustrated in FIG. 19A as a first operation screen. The operation screen G1 includes an image display area G10 and an operation area G11. Examples of what is displayed in the image display area G10 include an image of the subject's eye, the subject's eye information such as patient ID, measurement conditions, measurement result, operational mode that is currently used, a message for examination, a target position image for indicating the target position, and the like. In step S3, a message for examination, "Please adjust alignment with the control lever", is displayed. In the operation area G11, one or more button images, which can be designated by a touch operation, are displayed to control the measuring head 3. The image display area G10 and the operation area G11 are touch-operable areas.

(Step S4)

The main controller 201 judges whether an operation that has been performed is an operation on the operation unit 20 (lever operation using the operating lever 23) or a touch operation on the operation screen G1. When it is judged that an operation is performed on the operation unit 20 (Y in step S4), the process proceeds to step S5. When it is judged that no operation is performed on the operation unit 20, but a touch operation is performed on the operation screen G1 (N in step S4), the process proceeds to step S7.

(Step S5)

In step S4, when it is judged that an operation is performed on the operation unit 20 (Y in step S4), the measurement controller 201c sets the operation mode to the semi-automatic mode. In the semi-automatic mode, the measuring head 3 is aligned in response to the operation on the UI 10 or the operation unit 20. When the alignment error falls in a predetermined range, the alignment of the measuring head 3 is performed automatically.

(Step S6)

The measurement controller 201c performs the measurement of the subject's eye using the optical system, the alignment of which has been performed in step S5. Thereby, the process ends (END).

(Step S7)

When it is judged that a touch operation is performed on the UI 10 is step S4 (N in step S4), the measurement controller 201c sets the operation mode to the automatic mode. In the automatic mode, the measuring head 3 is aligned automatically.

That is, in response to the detection of the transition to the enabled state when the automatic mode is used, the measurement controller 201c controls the measuring head 3 in the automatic mode (step S7) or the semi-automatic mode (step S5).

(Step S8)

The measurement controller 201c performs the measurement of the subject's eye using the optical system, the alignment of which has been performed in step S7. Thereby, the process ends (END).

(Step S9)

When it is judged that the alignment mode that is currently applied is not the automatic mode in step S2 (N in step S2), that is, when it is judged that the alignment mode that is currently applied is the manual mode, the measurement controller 201c displays, on the UI 10, an operation screen G3 as illustrated in FIG. 20A as a second operation screen. In the image display area G10 of the operation screen G3, a message for examination, "Please adjust alignment with the lever and press the measurement switch" is displayed.

(Step S10)

The measurement controller 201c sets the operation mode to the manual mode. In the manual mode, the measuring head 3 is aligned in response to an operation on the UI 10 or the operation unit 20.

(Step S11)

Having received an instruction to start measurement by depression of the measurement switch 24b or a touch operation on the UI 10, the measurement controller 201c performs the measurement of the subject's eye using the optical system, the alignment of which has been performed in step S10. Thereby, the process ends (END).

(Step S12)

When it is detected that the operation on the operation unit 20 is disabled in step S1 (N in step S1), the measurement controller 201c judges whether the alignment mode that is currently used is the automatic mode. When it is judged that the alignment mode that is currently used is the automatic mode (Y in step S12), the process proceeds to step S13. When it is judged that the alignment mode that is currently used is not the automatic mode (N in step S12), the process proceeds to step S14.

(Step S13)

When it is judged that the alignment mode that is currently used is the automatic mode in step S12 (Y in step S12), the measurement controller 201c displays, on the UI 10, an operation screen G2 as illustrated in FIG. 19B as a third operation screen. In the image display area G10 of the operation screen G2, as a message for examination, "Please touch the pupil" is displayed. After that, the process returns to step S4.

(Step S14)

When it is judged that the alignment mode that is currently used is not the automatic mode in step S12 (N in step S12), that is, when it is judged that the alignment mode that is currently used is the manual mode, the measurement controller 201c displays, on the UI 10, an operation screen G4 as illustrated in FIG. 20B as a fourth operation screen. In the image display area G10 of the operation screen G4, a message for examination, "Please adjust the focus and touch the measurement site" is displayed. After that, the process returns to step S10.

The alignment mode is an example of the "operation mode" of the embodiment. The automatic mode is an example of the "first operation mode" of the embodiment. The manual mode is an example of the "second operation mode" of the embodiment. Steps S5 to S8 are an example of the "third operation mode" of the embodiment. Steps S14, S10, and S11 are an example of the "fourth operation mode" of the embodiment.

<Effects>

Described below are the effects of the ophthalmologic apparatus and the ophthalmologic apparatus system according to the embodiment.

According to the embodiment, the ophthalmologic apparatus (e.g., the ophthalmologic apparatus 1) is configured such that an operation unit (e.g., the operation unit 20) is attached thereto. The ophthalmologic apparatus includes a measuring head (e.g., the measuring head 3), a user interface (e.g., the UI 10), and a controller (e.g., the controller 200). The measuring head is configured to perform optical measurement of a subject's eye. The user interface is configured for performing an operation in relation to the optical measurement of the subject's eye. The controller is configured to detect whether operation on the operation unit is enabled or not, and perform at least display control for the user interface in different operation modes between an enabled state in which the operation on the operation unit is enabled and a disabled state in which the operation on the operation unit is disabled.

With this configuration, at least display control for the user interface is performed depending on a detection result as to whether the operation on the operation unit is enabled. Accordingly, the examiner or the like can perform an operation on the user interface or the operation unit without hesitation.

In the ophthalmologic apparatus according to an aspect of the embodiment, the controller may be configured to control at least the measuring head in a third operation mode in response to the detection of a transition to the enabled state when a first operation mode is being used. Further, the controller may be configured to control at least the measuring head in a fourth operation mode in response to the detection of a transition to the enabled state when a second operation mode is being used.

With this configuration, the measuring head is controlled according to the operation mode that is used when the operation on the operation unit becomes enabled. Thus, the examiner can proceed with an examination while performing easy and clear operation by changing the operation mode appropriately.

In the ophthalmologic apparatus according to an aspect of the embodiment, the first operation mode may be an automatic mode in which the measuring head is automatically aligned with respect to the subject's eye. The second operation mode may be a manual mode in which alignment is performed in response to an operation performed on the user interface. The third operation mode may be the automatic mode or a semi-automatic mode in which alignment is performed automatically when alignment error falls within a predetermined range in response to an operation performed on the user interface or the operation unit. The fourth operation mode may be the manual mode.

With this configuration, the operation mode can be switched among the automatic mode, the semi-automatic mode, and the manual mode. Thus, the measuring head can be controlled by an easy and clear operation for the examiner or the like.

Further, in the ophthalmologic apparatus according to an aspect of the embodiment, the controller may be configured to display different messages on the user interface between the enabled state and the disabled state.

With this configuration, the examiner or the like can be informed of whether the operation unit is enabled or not.

According to the embodiment, the ophthalmologic apparatus system includes an operation unit and the ophthalmologic apparatus according to any aspect of the embodiment described above.

With the ophthalmologic apparatus system having this configuration, the examiner or the like can perform an operation on the user interface or the operation unit without hesitation.

The operation unit (e.g., the operation unit 20) of the embodiment can be attached to an ophthalmologic apparatus (e.g., the ophthalmologic apparatus 1). The operation unit includes an operating lever (e.g., the operating lever 23), a support portion (e.g., the support portion 26), and a housing (e.g., the housing 40). The support portion is configured to tiltably support the operating lever. The housing accommodates at least part of the support portion. The operating lever protrudes upward from an opening (e.g., the opening 42a) formed in the upper surface of the housing. The periphery of the opening is provided with a protrusion (e.g., the protrusion 45) that protrudes upward.

With this configuration, the examiner who operates the operation unit at an arbitrary position can tilt the operating lever by hooking the protrusion with the bent little finger or the little finger ball of his/her hand used for manipulation. This facilitates the tilting of the operating lever about the little finger or the like hooked on the protrusion as a pivot. Thus, it is possible to maintain the operability of the ophthalmologic apparatus regardless of the position of the examiner.

In the operation unit of an aspect of the embodiment, the protrusion may be provided over the entire circumference of the opening.

With this configuration, the little finger or the like can be hooked on the protrusion regardless of the direction in which the operating lever is gripped. Thus, it is possible to maintain the operability of the ophthalmologic apparatus for the examiner at any position.

In the operation unit of an aspect of the embodiment, at least part of the housing and the protrusion may be integrally formed.

With this configuration, the protrusion can be provided at a low cost.

In the operation unit of an aspect of the embodiment, the protrusion may have an outer shape of a non-perfect circle as viewed from the above.

With this configuration, the examiner can easily hook the protrusion with the bent little finger or the little finger ball of his/her hand used for manipulation.

In the operation unit of an aspect of the embodiment, the protrusion may be configured to be rotatable about an axis passing through the opening.

With this configuration, by rotating the protrusion for easy operation, the examiner can tilt the operating lever at any position with optimum operability In the operation unit of an aspect of the embodiment, the height of the protrusion may be 5 mm or more and 10 mm or less in the lowest portion thereof.

With this configuration, the examiner can operate the ophthalmologic apparatus without hindrance to tilt the operating lever while hooking the little finger or the little finger ball of his/her hand used for manipulation on the protrusion.

In the operation unit of an aspect of the embodiment, the height of the lowest portion may be 7.5 mm or more and 8 mm or less.

With this configuration, the examiner can operate the ophthalmologic apparatus without hindrance to tilting the operating lever while hooking the little finger or the little finger ball of his/her hand used for manipulation on the protrusion.

According to the embodiment, the ophthalmologic apparatus system (e.g., the ophthalmologic apparatus system 100) includes an ophthalmologic apparatus and an operation unit according to any aspect of the embodiment described above.

With the ophthalmologic apparatus system having this configuration, the operability of the ophthalmologic apparatus can be maintained regardless of the position of the subject.

The operation unit (e.g., the operation unit 20) of the embodiment can be attached to an ophthalmologic apparatus (e.g., the ophthalmologic apparatus 1). The operation unit includes a housing (e.g., the housing 40) and one or more connection members (e.g., the connection hooks 35). The housing accommodates at least part of the operation section for operating the ophthalmologic apparatus (e.g., the control lever 22, the first potentiometer 27a, the second potentiometer 27b, the rotary encoder 27c, the first switch 30, the second switch 31, the switch operation detectors 27d, 30a, and 31a). The connection member(s) include(s) a contact portion that is in contact with a portion of the bottom surface of the ophthalmologic apparatus to which the operation unit is being attached. The connection member(s) is/are provided so as to protrude with respect to the housing.

With this configuration, the upper surface of the connection member(s) is in contact with a portion of the bottom surface of the housing of the ophthalmologic apparatus. Accordingly, the weight of the ophthalmologic apparatus is applied to the upper surface of the connection member(s), thereby restricting the movement of the operation unit. Thus, the operation unit, which can be attached to an ophthalmologic apparatus as an attachment, achieves space saving as well as maintaining its operability.

The operation unit (e.g., the operation unit 20) of the embodiment can be attached to an ophthalmologic apparatus (e.g., the ophthalmologic apparatus 1). The operation unit includes a housing (e.g., the housing 40) and one or more connection members (e.g., the connection hooks 35). The housing accommodates at least part of the operation unit for operating the ophthalmologic apparatus (e.g., the control lever 22, the first potentiometer 27a, the second potentiometer 27b, the rotary encoder 27c, the first switch 30, the second switch 31, the switch operation detectors 27d, 30a, and 31*a*). The connection member(s) include(s) an engagement portion that engages the ophthalmologic apparatus. The connection member(s) is/are provided so as to protrude with respect to the housing.

With this configuration, the connection member(s) is/are engaged with the ophthalmologic apparatus, thereby restricting the movement of the operation unit. Thus, the operation unit, which can be attached to an ophthalmologic apparatus as an attachment, achieves space saving as well as maintaining its operability.

The operation unit (e.g., the operation unit 20) of the embodiment can be attached to an ophthalmologic apparatus (e.g., the ophthalmologic apparatus 1). The operation unit includes a housing (e.g., the housing 40) and one or more connection members (e.g., the connection hooks 35). The housing accommodates at least part of the operation section for operating the ophthalmologic apparatus (e.g., the control lever 22, the first potentiometer 27*a*, the second potentiometer 27*b*, the rotary encoder 27*c*, the first switch 30, the second switch 31, the switch operation detectors 27*d*, 30*a*, and 31*a*). The connection member(s) include(s) a contact portion and an engagement portion. The connection member(s) is/are provided so as to protrude with respect to the housing. The contact portion is in contact with a portion of the bottom surface of the ophthalmologic apparatus to which the operation unit is being attached. The engagement portion engages the ophthalmologic apparatus.

With this configuration, the upper surface of the connection member(s) is in contact with a portion of the bottom surface of the housing of the ophthalmologic apparatus. Accordingly, the weight of the ophthalmologic apparatus is applied to the upper surface of the connection member(s), thereby restricting the movement of the operation unit. Besides, the connection member(s) is/are engaged with the ophthalmologic apparatus, thereby restricting the movement of the operation unit. Thus, the operation unit is attached to the ophthalmologic apparatus more firmly. Further, the operation unit, which can be attached to the ophthalmologic apparatus as an attachment, achieves space saving as well as maintaining its operability.

In the operation unit of an aspect of the embodiment, a through region, which penetrates through the connection member(s) from the upper surface to the lower surface, may be formed in at least one of the connection member(s).

With this configuration, for example, the operation unit can be engaged with the ophthalmologic apparatus by using the through region formed in the connection member(s). Thus, the operation unit can be firmly attached to the ophthalmologic apparatus in an easy way.

In the operation unit of an aspect of the embodiment, the through region may be a through hole (e.g., the through hole 35*a*), in which a leg projecting downward from the bottom surface of the housing of the ophthalmologic apparatus is inserted.

With this configuration, a leg provided on the bottom surface of the housing of the ophthalmologic apparatus is inserted into the through hole. Thereby, the operation unit engages the ophthalmologic apparatus. Thus, the operation unit can be firmly attached to the ophthalmologic apparatus in an easy way.

The operation unit of an aspect of the embodiment may further include a cover (e.g., the cover 35*b*) configured to cover at least part of the edge of the through region.

With this configuration, the cover serves as an edge protection member and prevents the scratching of the leg of the ophthalmologic apparatus inserted into the through region. The cover also serves as a leg holding member and holds the leg of the ophthalmologic apparatus inserted into the through region, thereby restricting the movement of the operation unit.

The operation unit of an aspect of the embodiment may further include one or more slip stopper(s) (e.g., the slip stopper 35*c*) arranged on the lower surface of at least one of the connection member(s).

With this configuration, the lower surface of the slip stopper is in contact with the supporting surface of the operation unit. Thus, the movement of the operation unit is restricted.

The operation unit of an aspect of the embodiment may further include one or more cushioning member(s) (e.g., the cushioning member 35*d*) arranged on the upper surface of at least one of the connection member(s).

With this configuration, the upper surface of the cushioning member is in contact with the bottom surface of the housing of the ophthalmologic apparatus, to which the operation unit is being attached. Thus, the ophthalmologic apparatus and the operation unit can be protected.

The operation unit of an aspect of the embodiment may further include a cushioning member (e.g., the cushioning member 36) arranged on a surface facing the ophthalmologic apparatus, to which the operation unit is being attached.

With this configuration, the cushioning member is in contact with the housing of the ophthalmologic apparatus, to which the operation unit is being attached. Thus, the ophthalmologic apparatus and the operation unit can be protected.

According to the embodiment, the ophthalmologic apparatus system (e.g., the ophthalmologic apparatus system 100) includes an ophthalmologic apparatus and an operation unit according to any aspect of the embodiment described above.

The ophthalmologic apparatus system having such a configuration can maintain the operability of the ophthalmologic apparatus to which the operation unit is attached as an attachment as well as achieving space saving.

<Modification>

The embodiments described above are mere examples for embodying or carrying out the present invention, and therefore susceptible to several modifications and variations (omission, substitution, addition, etc.), all coming within the scope of the invention.

In the above embodiment, when the connection hooks 35 include the contact portion, the contact portion may be at least part of a recess formed in the upper surface of the connection hooks 35. In other words, the contact portion may be configured in the recess formed in the upper surface of the connection hooks 35 such that the contact portion in contact with a portion of the bottom surface of the ophthalmologic apparatus 1. With this configuration, since the position of the portion of the bottom surface of the ophthalmologic apparatus 1 in contact with the contact portion is substantially fixed to the recess. Thus, the movement of the ophthalmologic apparatus 1 can be restricted.

While, in the above embodiment, the operation unit 20 is described as being attached to the front side of the ophthalmologic apparatus 1, the embodiment is not so limited. For example, the operation unit 20 may be attached to the side or the like of the ophthalmologic apparatus 1.

Regarding the operation unit 20 of the above embodiment, the control lever 22 is described as being tiltable; however, the embodiment is not so limited. The operation unit 20 may be configured to allow only the pressing of one or more switches.

The outer shape of the operation unit 20 of the embodiment (in particular, the shape of the upper surface) is not limited to those described in the above embodiment. The operation unit of the embodiment is not limited by the shape of the connection hooks. Also, the shapes of vertical and horizontal cross sections of the protrusion 45 are not so limited.

While, in the above embodiment, the protrusion 45 is described as being provided to the operation unit 20 that is attachable to the ophthalmologic apparatus 1, the embodiment is not so limited. For example, the protrusion 45 of the embodiment may be provided to an ophthalmologic apparatus having an operating lever.

The operation unit 20 of the embodiment may be configured to be detachably attached to the ophthalmologic apparatus 1.

While certain embodiments have been described, these embodiments have been presented by way of example only, and are not intended to limit the scope of the inventions. Indeed, the novel embodiments described herein may be embodied in a variety of other forms; further, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus configured such that an operation unit is attached thereto, the ophthalmologic apparatus comprising:
   a measuring head configured to perform optical measurement of a subject's eye;
   a user interface configured for performing an operation in relation to the optical measurement of the subject's eye; and
   a controller configured to detect whether an operation on the operation unit is enabled, and perform at least display control for the user interface in different operation modes between an enabled state in which the operation on the operation unit is enabled and a disabled state in which the operation on the operation unit is disabled.

2. The ophthalmologic apparatus of claim 1, wherein the controller is further configured to
   control at least the measuring head in a third operation mode in response to detection of a transition to the enabled state when a first operation mode is being used, and
   control at least the measuring head in a fourth operation mode in response to detection of a transition to the enabled state when a second operation mode is being used.

3. The ophthalmologic apparatus of claim 2, wherein
   the first operation mode is an automatic mode in which the measuring head is automatically aligned with respect to the subject's eye,
   the second operation mode is a manual mode in which the measuring head is aligned in response to an operation performed on the user interface,
   the third operation mode is the automatic mode, or a semi-automatic mode in which the measuring head is automatically aligned when alignment error falls within a predetermined range in response to an operation performed on the user interface or the operation unit, and
   the fourth operation mode is the manual mode.

4. The ophthalmologic apparatus of claim 1, wherein the controller is further configured to display different messages on the user interface between the enabled state and the disabled state.

5. An ophthalmologic apparatus system, comprising
   the operation unit; and
   the ophthalmologic apparatus of claim 1.

6. The ophthalmologic apparatus system of claim 5, wherein
   the operation unit includes
      an operating lever,
      a support portion configured to support the operating lever in a tiltable manner, and
      a housing configured to accommodate at least part of the support portion, wherein
   the operating lever protrudes upward from an opening formed in an upper surface of the housing, and
   a periphery of the opening is provided with a protrusion that protrudes upward.

7. The ophthalmologic apparatus system of claim 5, wherein the operation unit includes
   a housing configured to accommodate at least part of an operation section for operating the ophthalmologic apparatus, and
   at least one connection member including a contact portion that is in contact with a portion of a bottom surface of the ophthalmologic apparatus to which the operation unit is being attached, and protruding with respect to the housing.

8. The ophthalmologic apparatus system of claim 5, wherein the operation unit includes
   a housing configured to accommodate at least part of an operation section for operating the ophthalmologic apparatus, and
   at least one connection member including an engagement portion that engages the ophthalmologic apparatus and protruding with respect to the housing.

9. The ophthalmologic apparatus system of claim 5, wherein the operation unit includes
   a housing configured to accommodate at least part of an operation section for operating the ophthalmologic apparatus, and
   at least one connection member protruding with respect to the housing, and including
      a contact portion that is in contact with a portion of a bottom surface of the ophthalmologic apparatus to which the operation unit is being attached, and
      an engagement portion that engages the ophthalmologic apparatus.

* * * * *